(12) United States Patent
Jalkanen et al.

(10) Patent No.: US 10,293,030 B2
(45) Date of Patent: May 21, 2019

(54) LYOPHILISED PHARMACEUTICAL FORMULATION AND ITS USE

(71) Applicant: FARON PHARMACEUTICALS OY, Turku (FI)

(72) Inventors: Markku Jalkanen, Piispanristi (FI); Mikael Maksimow, Turku (FI); Ilse Piippo, Parainen (FI)

(73) Assignee: Faron Pharmaceuticals Oy, Turku (FI)

( * ) Notice: Subject to any disclaimer, the term of this patent is extended or adjusted under 35 U.S.C. 154(b) by 131 days.

(21) Appl. No.: 15/355,691

(22) Filed: Nov. 18, 2016

(65) Prior Publication Data
US 2017/0246254 A1    Aug. 31, 2017

(30) Foreign Application Priority Data

Feb. 29, 2016  (FI) ................................. 20165153

(51) Int. Cl.
| A61K 38/21 | (2006.01) |
| A61K 9/00 | (2006.01) |
| A61K 9/19 | (2006.01) |
| A61K 47/20 | (2006.01) |
| A61K 47/26 | (2006.01) |
| C07K 14/565 | (2006.01) |

(52) U.S. Cl.
CPC .......... *A61K 38/215* (2013.01); *A61K 9/0019* (2013.01); *A61K 9/19* (2013.01); *A61K 47/20* (2013.01); *A61K 47/26* (2013.01); *C07K 14/565* (2013.01)

(58) Field of Classification Search
CPC ...... A61K 38/215; A61K 9/0019; A61K 9/19; A61K 47/26; C07K 14/565
See application file for complete search history.

(56) References Cited

U.S. PATENT DOCUMENTS 7,740,884 B2 *  6/2010  Samaritani ........... A61K 9/0019
                                                424/198.1
2006/0051320 A1 *  3/2006  Shameem ............ A61K 9/0019
                                                424/85.4

FOREIGN PATENT DOCUMENTS

| EP | 0 150 067 A2 | 7/1985 |
| EP | 0 270 799 A1 | 6/1988 |
| EP | 0 726 310 A1 | 8/1996 |
| EP | 1 608 400 B1 | 6/2010 |
| WO | 99/15193 A1 | 4/1999 |
| WO | 2004/006756 A2 | 1/2004 |
| WO | 2004/100979 A2 | 11/2004 |
| WO | 2012/071366 A1 | 5/2012 |

OTHER PUBLICATIONS

Search Report dated Jun. 14, 2016 by the Finnish Patent Office in counterpart application No. 20165153 (2 pages).
Communication of Acceptance dated Oct. 28, 2016 by the Finnish Patent Office in counterpart application No. 20165153 (3 pages).
Bellingan, G., et al. The effect of intravenous interferon-beta-1a (FP-1201) on lung CD73 expression and on acute respiratory distress syndrome mortality: an open-label study. Lancet Respir. Med. 2014, vol. 2 (10 pages).
Jalkanen, M., et al. A phase I/II clinical trial of FP-1201 (a novel anti-inflammatory interferon-beta and an inhibitor of vascular leakage) reduces mortality in ALI/ARDs. American Journal of Respiratory and Critical Care Medicine, 2012, vol. 185, No. Abstract (1 page).
Jalkanen, S. New molecules controlling endothelial barrier. Critical Care (Mar. 16, 2015) vol. 19, No. Suppl. 1, Abstract (1 page).
Kiss, J., et al. IFN-β protects from vascular leakage via upregulation of CD73. Eur. J. Immunol., 2007, vol. 37 (5 pages).
Search Report and Written Opinion dated May 19, 2017 in PCT Application No. PCT/FI2017/050128 (11 pages).

* cited by examiner

*Primary Examiner* — Robert S Landsman
*Assistant Examiner* — Bruce D. Hissong
(74) *Attorney, Agent, or Firm* — Rothwell, Figg, Ernst & Manbeck, P.C.

(57) ABSTRACT

A pharmaceutical formulation in a lyophilised form, which comprises pharmacologically effective amount of interferon beta-1a as an active ingredient, disaccharides as a bulking agent and a non-ionic surfactant. After reconstitution, the composition can be administered intravenously.

23 Claims, 12 Drawing Sheets

| Analytical procedure | Acceptance criteria | Unit | Times (hour) | | |
|---|---|---|---|---|---|
| | | | 0 | 24 | 48 |
| Appearance and description | | | | | |
| Clarity (instrumental) | Clear (≤ Ref. I) | N/A | | Clear (≈ WFI) | |
| Colour (b-scale, Ph. Eur.) | Report result (Target: Colourless (≤ B9)) | N/A | | Colourless (< B9) | |
| Colour (y-scale, Ph. Eur.) | Report result (Target Colourless (< Y7)) | N/A | | Colourless (< Y7) | |
| Visible particles | Free or practically free of visible particles | N/A | Free of visible particles [a] | | Free of visible particles |
| Identity | | | | | |
| Peptide mapping Lys-C | Corresponds to standard | N/A | | Corresponds | |

Fig. 16

| Analytical procedure | Acceptance criteria | Unit | Time [hour] | | |
|---|---|---|---|---|---|
| | | | 0 | 24 | 48 |
| Content | | | | | |
| RP-HPLC content IFN beta-1 a protein | Report result (Target: 12.3 ± 2.3 µg/mL) | [µg/mL] | 11.9 | 12.0 | 11.1 |
| Activity/ Potency | | | | | |
| Bioassay Potency | ≥ 150 MIU/mg | Potency: [MIU/mg] (Activity [MIU/mL]) | | 227 (2.7) | |
| Purity and Impurities | | | | | |
| SE-HPLC HMWS | Report result (Target: ≤ 2 Area-%) | [Area-%] | | < 0.8 | |
| Peptide Mapping Oxidized IFN beta-1 a | Report result (Target: ≤ 6 Area-%) | [Area-%] | 3.2 | 3.5 | 3.4 |
| Deamidation | Report result | [Area-%] | 41.2 | 44.9 | 48.7 |
| General tests | | | | | |
| pH | Report result (Target: 6.5 ± 0.2) | N/A | | 6.6 | |
| Osmolality | Report result (Target: 340 ± 50 mOsmol/kg) | [mOsmol/kg] | 349 | 345 | 332 |

Fig. 17

| Analytical procedure | Acceptance criteria | Unit | Time [hours] | | |
|---|---|---|---|---|---|
| | | | 0 | 24 | 48 |
| Sub-visible particles | ≥ 10 μm: ≤ 6000 particles/container | [Particles/ container] | 155 | 331 | 1021 |
| | ≥ 25 μm: ≤ 600 particles/container | | 8 | 6 | 8 |

Fig. 18

| Analytical procedure | Acceptance criteria | Unit | Result |
|---|---|---|---|
| Delivered WFI from the syringe | | | |
| Weight of pre-filled syringe (value 1) | Report result | [g] | 7.068 |
| Weight of empty syringe (value 2) | Report result | [g] | 6.070 |
| Density WFI | Report result | [g/mL] | 0.9981 |
| Amount WFI (result 1) | Report result | [mL] | 1.000 |
| Volume DP after reconstitution | | | |
| Weight of vial with WFI (value 3) | Report result | [g] | 6.449 |
| Weight of empty vial (value 4) | Report result | [g] | 5.446 |
| Weight of dried empty vial (value 5) | Report result | [g] | 5.395 |
| Density reconstituted solution-vial | Report result | [g/mL] | 1.0266 |
| Sample solution real volume (result 2) | Report result | [mL] | 0.977 |
| Sample solution total volume (result 3) | Report result | [mL] | 1.026 |
| Amount of reconstituted DP delivered from the syringe without MIXJECT™ | | | |
| Weight of syringe with DP (value 6) | Report result | [g] | 7.075 |
| Weight of empty syringe (value 7) | Report result | [g] | 6.039 |
| Density reconstituted solution-syringe | Report result | [g/mL] | 1.0247 |
| Volume delivered without MIXJECT™ (result 4) | Report result | [mL] | 1.011 |

Fig. 19

| Analytical procedure | Acceptance criteria | Unit | Result |
|---|---|---|---|
| Amount of reconstituted DP delivered from the syringe with MIXJECT™ | | | |
| Weight of syringe with DP (value 8) | Report result | [g] | 8.095 |
| Weight of empty syringe (value 9) | Report result | [g] | 7.081 |
| Density reconstituted solution-syringe | Report result | [g/mL] | 1.0252 |
| Volume delivered with MIXJECT™ (result 5) | Report result | [mL] | 0.989 |
| Loss of IFN beta-1a protein during application | | | |
| Content of IFN beta-1a from vial | Report result | [μg/mL] | 11.9<br>(result from SP1241, 0 hours ) |
| Volume of reconstituted DP solution in vial | Report result | [mL] | 1.026<br>(result 3, SP1241/4) |
| IFN beta-1a amount in vial | Report result | [μg] | 12.2<br>(11.9 μg/mL x 1.026 mL) |
| Content of IFN beta-1a from syringe | Report result | [μg/mL] | 11.1<br>(result from SP1241/3, 48 hours) |
| Volume of reconstituted DP solution delivered from the syringe | Report result | [mL] | 1.011<br>(result 4, SP1241/4) |
| IFN beta-1a amount delivered from syringe | Report result | [μg] | 11.2<br>(11.1 μg/mL x 1.011 mL) |
| Loss of IFN beta-1a protein during application | Report result | [μg] | 1.0<br>(12.2 μg in vial - 11.2 μg delivered from syringe) |

under# LYOPHILISED PHARMACEUTICAL FORMULATION AND ITS USE

CROSS-REFERENCE TO RELATED APPLICATIONS

The present application is related to and claims priority to Finnish patent application no. 20165153 filed on 29 Feb. 2016. This application is incorporated herein in its entirety.

FIELD OF THE INVENTION

The present invention relates to a lyophilised pharmaceutical formulation of interferon beta-1a and uses of the formulation.

BACKGROUND OF THE INVENTION

Interferon beta-1a is an interferon beta 1 agonist with the ability to up-regulate CD73, a molecule which yields anti-inflammatory adenosine, which enhances endothelial barrier function and leads to the prevention of vascular leakage, the predominant pathophysiological event in ARDS. Vascular leakage in ARDS allows plasma exudation into the alveolar space leading to potentially life-threatening hypoxaemia. Interferon beta-1a has the potential to reduce the impact of ARDS by reducing vascular leakage, but is not limited to this example.

As with all protein based pharmaceuticals, one major obstacle that must be overcome in the use of interferon beta (IFN-beta) as a therapeutic agent is the loss of pharmaceutical utility that can result from its instability in pharmaceutical formulations. Physical instabilities that threaten polypeptide activity and efficacy in pharmaceutical formulations include denaturation and formation of insoluble aggregates, while chemical instabilities include e.g. hydrolysis, oxidation and deamidation. Some of these changes are known to lead to the loss or reduction of the pharmaceutical bioactivity of the protein of interest. When small amounts of hormone peptides are administered, it is also crucial that the patient is guaranteed to receive the right dosing. Due to high lipophilic amino acid residue content in IFN-beta, it adheres to container surfaces and form aggregates, resulting in losses of active pharmaceutical ingredient.

Another requirement, especially for the drug products for use in the treatment of ARDS, is that the drug product has to be available in an emergency. Consequently, there is a need for stable lyophilised pharmaceutical formulations comprising IFN-beta 1a having long shelf life and preserving their pharmaceutical utility, and especially if freeze-dried, requiring careful control of dosing and in use stability during administration. These requirements are necessary for compounds administered intravenously, as the patient gets exposed to the drug instantly.

SUMMARY OF THE INVENTION

The object of the invention is to provide a stable pharmaceutical formulation in a lyophilised form comprising interferon beta-1a.

It is especially an object of the present invention to provide pharmaceutical formulation in lyophilised form comprising interferon beta-1a, which enables good recovery of Interferon beta-1a after reconstitution.

Further object of the present invention is to provide a pharmaceutical formulation for prevention and treatment of vascular-endothelial diseases in humans with intravenous administration. Especially, the object of the present invention is to provide a pharmaceutical formulation for use as a treatment to prevent vascular leakage in patients having Acute Respiratory Distress Syndrome (ARDS), but not limited to this condition.

In order to achieve among others the objects presented above, the invention is characterized by what is presented in the enclosed independent claims.

A typical pharmaceutical formulation according to the invention in a lyophilised form comprises pharmacologically effective amount of interferon beta-1a as an active ingredient, disaccharides as a bulking agent, and a non-ionic surfactant.

According to the invention, interferon beta-1a may be formulated as a lyophilisate, which can be reconstituted to give an aqueous solution with pharmacologically effective and correct amounts of interferon beta-1a for delivery to a patient. Thus, the invention also provides an aqueous pharmaceutical composition obtained by reconstituting a lyophilised formulation.

The aqueous compositions of the invention with pharmacologically effective amounts of interferon beta-1a are particularly suitable for intravenous administration.

The invention further concerns a delivery device including the aqueous pharmaceutical composition of the invention.

The invention further concerns a pre-filled syringe including the aqueous pharmaceutical composition of the invention.

The invention further concerns a lyophilised formulation or an aqueous pharmaceutical composition according to the invention for prevention and/or treatment of vascular-endothelial diseases in humans.

More specifically, the invention concerns a lyophilised formulation or an aqueous pharmaceutical composition according to the invention for prevention and/or treatment of vascular-endothelial diseases in humans with intravenous administration, wherein interferon beta-1a is administrated into the patient at 7.5-12.5 µg/dose, or at 2.0-12.5 µg/dose if the patient is less than 18 years in age.

The invention further concerns a lyophilised formulation or an aqueous pharmaceutical composition according to the invention for use in the prevention vascular leakage in acute respiratory distress syndrome (ARDS), systemic inflammatory response syndrome (SIRS) and other traumatic conditions.

The invention further concerns a lyophilised formulation or an aqueous pharmaceutical composition according to the invention for use in the prevention and/or treatment of ischemia-reperfusion injury in vascular or cardiac surgery and organ transplantation, or for use in ischemic pre-conditioning prior to major vascular or cardiac surgery and organ transplantation.

The invention further concerns a lyophilised formulation or an aqueous pharmaceutical composition according to the invention for use in the prevention and/or treatment of acute pancreatitis and acute kidney injury.

The invention further concerns a lyophilised formulation or an aqueous pharmaceutical composition according to the invention for use in severe life threatening viral infections such as EBOLA, MERS, influenza such as avian flu, and other similar conditions leading to a systemic inflammatory response syndrome (SIRS) and dysfunction of central organs.

The invention further concerns a lyophilised formulation or an aqueous pharmaceutical composition according to the invention for use in severe bacterial pneumonia and sepsis leading to a systemic inflammatory response syndrome (SIRS) and multi-organ failure (MOF), or for use in the prevention and/or treatment of MOF.

BRIEF DESCRIPTION OF THE DRAWINGS

FIGS. 16-20 show compilation of the results of the stability study.

DETAILED DESCRIPTION OF THE INVENTION

Terms and Definitions

Figures 1, 2:
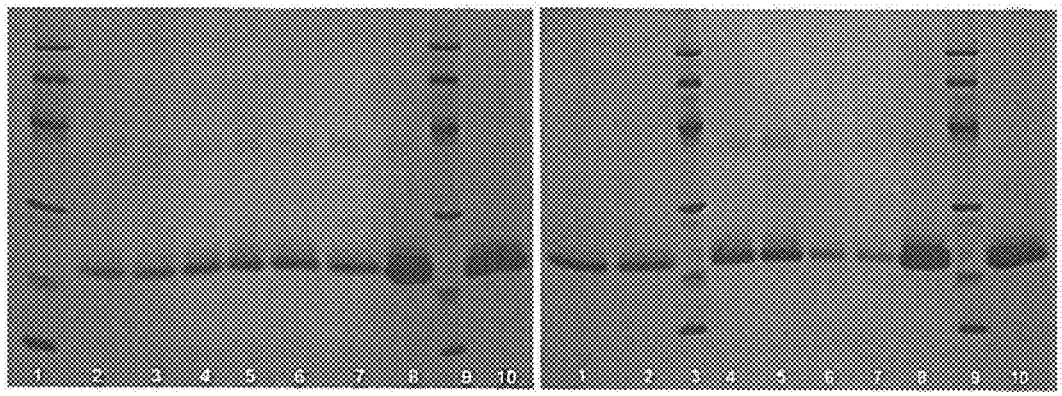
FIGS. 1-4 show non-reducing SDS-PAGE of reconstituted INF-beta 1a lyophilisates. See formulation study A of the experimental part.

In this application the terms "interferon beta-1a", "INF-beta 1a" and "INF-β1a" are interchangeable and they are used as synonyms to each other.

The expression "pharmacologically effective amount" is meant to include any amount of Interferon beta-1a that is sufficient to bring about a desired therapeutically result.

The term "treatment" or "treating" shall be understood to include complete curing of a disease as well as amelioration or alleviation of said disease.

The term "prevention" shall be understood to include complete prevention, prophylaxis, as well as lowering the individual's risk of falling ill with said disease or disorder.

The term "patient" or "individual" refers to a human.

The term "lyophilize" with regard to pharmaceutical formulations of the invention is intended to refer to freeze drying of an aqueous solution of the formulation. The term "lyophilisate" refers to the product of lyophilisation. The term "reconstitution" refers to dissolution of the lyophilisate for achieving an aqueous solution.

The term "intravenous" or 'IV' administration refers to administration within the blood vessels or lymphatics.

Embodiments of the Invention

The present invention is directed to Interferon beta-1a pharmaceutical formulation with increased stability and a substantially complete recovery of interferon beta-1a after reconstitution. A pharmaceutical formulation in a lyophilized form according to the invention comprises at least pharmacologically effective amount of interferon beta-1a as an active ingredient, disaccharide or disaccharides as a bulking agent, and a non-ionic surfactant.

It has been observed that the combination of disaccharides as a bulking agent and non-ionic surfactant, such as polysorbate or polyethylene glycol (PEG), is needed for the substantially complete recovery of Interferon beta-1a after freeze drying and reconstitution and for stabilization of Interferon beta-1a against degradation in the freeze-dried state during storage. The lyophilized formulation according to the invention is stable at temperature of 2-8° C. for at least 24 months, preferably at least 30 months and more preferably even a period of 36 months. It has also been observed that the Interferon beta-1a of the lyophilized formulation retains its activity even when stored at room temperature (25-30° C.±2° C.). Consequently, the lyophilized formulation according to the invention has storage stability at room temperature at least six months, preferably at least 12 months and more preferably even a period of 24 months.

Non-ionic surfactants, such as polysorbate or polyethylene glycol (PEG), are used for both preventing surface adsorption and as stabilizers against protein aggregation. The surfactant is especially needed to prevent loss of INF-beta 1a during freeze-drying and reconstitution. A substantially complete recovery of INF-beta 1a after freeze-drying and reconstitution may be obtained by using polysorbate or PEG as a surfactant. After reconstitution of the lyophilisate, the recovery of interferon beta-1a content may be over 85%, preferably over 90% and even more preferably 95%. The substantially complete recovery after reconstitution is important since a single intravenous dose of the interferon beta-1a administrated into the patent is small, and therefore it is crucial that the patient is guaranteed to receive the right dosing.

According to one embodiment of the invention a non-ionic surfactant may be polysorbate or PEG. According to one preferred embodiment of the invention, the surfactant is polysorbate. The polysorbate may be polysorbate 20, polysorbate 40, polysorbate 60, polysorbate 80 or any other polysorbate. In a preferred embodiment of the invention polysorbate may be polysorbate 20, also called as Tween 20. According to one embodiment of the invention, the lyophilized formulation comprises 0.9-2 weight-%, preferably 1-1.5 weight-%, and more preferably 1.1-1.3 weight-% of a surfactant, such as polysorbate or PEG/vial, based on the total weight of the lyophilized formulation.

The amounts of the formulation components are presented per one vial in the current application; a single vial includes a single dose of the pharmaceutical formulation of the invention in a lyophilised form.

In a preferred embodiment of the invention disaccharides are selected from trehalose, sucrose and combination thereof. It has been observed that trehalose dihydrate or sucrose is a most suitable bulking agent for providing bulk to the formulation and for stabilization of INF-beta 1a against degradation in the freeze-dried state during storage. According to one preferred embodiment, trehalose dihydrate is used as a bulking agent. According to one embodiment of the invention, the lyophilized formulation comprises 50-80 weight-%, preferably 60-75 weight-%, and more preferably 63-67 weight-% of disaccharides/vial, based on the total weight of the lyophilized formulation.

According to one preferred embodiment of the invention, the lyophilized formulation comprises pharmacologically effective amount of interferon beta-1a as an active ingredient, disaccharides as a bulking agent, a non-ionic surfactant, a buffering agent for maintaining a pH of about 5.5 to 7.5 after reconstitution of the lyophilisate, and preferably an antioxidant.

According to one embodiment of the invention, the lyophilized formulation further comprises a suitable buffering agent for maintaining a pH of about 5.5 to 7.5, preferably about 6.0 to 7.0 and more preferably about 6.3 to 6.7 after reconstitution of the lyophilisate. A buffering agent of the formulation according to the invention may be selected a group comprising of disodium phosphate dihydrate, sodium dihydrogen phosphate dihydrate, trisodium citrate dihydrate or combination thereof. The buffering agents in the formulation may be selected on the basis of the target pH and the combination and the ratio of the individual agents may be varied.

According to one embodiment of the invention, the lyophilized formulation further comprises an antioxidant. According to one preferred embodiment of the invention, the lyophilized formulation comprises methionine as an antioxidant for protecting the formulation against oxidation. The methionine may be DL-methionine or L-methionine. According to an embodiment of the invention methionine may already be included in interferon beta-1a drug substance.

According to one embodiment of the invention, a pharmaceutical formulation in a lyophilized form comprises
 at least pharmacologically effective amount of interferon beta-1a as an active ingredient,
 0.5 to 1.0 mg/vial, preferably 0.6 to 0.8 mg/vial of a non-ionic surfactant, such as polysorbate or PEG,
 to 50 mg/vial, preferably 35 to 40 mg/vial of trehalose dihydrate or sucrose,
 to 28 mg/vial, preferably 18 to 22 mg/vial of a combination of the buffering agents, and
 0.1 to 0.3 mg/vial, preferably 0.17 to 0.23 mg/vial of antioxidant.

The formulation according to the invention comprises pharmacologically effective amount of interferon beta-1a. Interferon beta-1a is preferably recombinant human interferon beta-1a. By recombinantly produced IFN-beta-1a is intended IFN-beta 1a that has comparable biological activity to mature native IFN-beta 1a and that has been prepared by recombinant DNA techniques. According to one embodiment of the invention, the interferon beta-1a drug substance may contain insoluble aggregates and the drug substance is purified to remove these existent insoluble aggregates before compounding the formulation. According to one preferred embodiment of the invention 95-100% of the IFN-beta 1a will be in a monomeric form for providing biological activity of the interferon beta-1a and a good solubility during reconstitution. Biological activity (potency) of the interferon beta-1a should be higher than 150 MIU/mg (MIU=million international units).

In the formulations encompassed by the invention, interferon beta-1a amount in a single intravenous dosage form may be varied between about 2.0 µg and 15 µg.

The content of residual moisture of the lyophilisated formulation according to the invention may not be more than 5% by weight for promoting storage stability of the lyophilised formulation. According to an embodiment, residual moisture content is in the range of about 1-5% and preferably about 1-4% by weight. For achieving the required limit for the content of the free residual water without denaturation of the protein, the lyophilisation cycle has to be optimised. According to an embodiment of the invention it has been observed that about 30-35 hours, preferably about 31 hours freeze-drying cycle is optimal for the formulation of the invention, as presented in the experimental part.

According to one embodiment of the invention the lyophilised formulation comprises
 interferon beta-1a as active ingredient,
 trehalose dihydrate or sucrose as a bulking agent,
 disodium phosphate dihydrate, sodium dihydrogen phosphate dihydrate, trisodium citrate dihydrate and any combination thereof as a buffering agent,
 polysorbate or polyethylene glycol as a surfactant, and
 methionine as an antioxidant.

More specifically, the lyophilised formulation according to one preferred embodiment comprises
 interferon beta-1a, preferably recombinant human interferon beta-1a, as active ingredient,
 trehalose dihydrate as a bulking agent,
 a combination of disodium phosphate dihydrate, sodium dihydrogen phosphate dihydrate and trisodium citrate dihydrate as a buffering agent,
 polysorbate 20 as a surfactant, and
 methionine as an antioxidant.

Typically, the lyophilised formulation according to the invention is prepared from an aqueous solution having a pH of 5.5-7.5 and comprising pharmacologically effective amount of interferon beta-1a as an active ingredient, disaccharides as a bulking agent, and a non-ionic surfactant. In a preferred embodiment of the invention the lyophilised formulation according to the invention is prepared from an aqueous solution having a pH of 5.5-7.5, preferably of 6.0 to 7.0, and comprising
 pharmacologically effective amount of interferon beta-1a, preferably recombinant human interferon beta-1a, as an active ingredient,
 trehalose dihydrate or sucrose as a bulking agent,
 polysorbate or PEG as a surfactant,
 disodium phosphate dihydrate, sodium dihydrogen phosphate dihydrate, trisodium citrate hydrate and any combination thereof as a buffering agent, and
 methionine as an antioxidant.

According to an embodiment of the invention the lyophilised formulation according to the invention is prepared from an aqueous solution comprises 0.05-0.15% (w/v) polysorbate or PEG, preferably polysorbate, and 2-6% (w/v) trehalose dihydrate or sucrose. According to one preferred embodiment of the invention the lyophilised formulation is prepared from an aqueous solution comprises about 0.1% (w/v) polysorbate or PEG, preferably polysorbate, and about 5% (w/v) trehalose dihydrate.

A method for preparing a lyophilisate according to the invention comprising the steps of preparing an aqueous solution comprising at least interferon beta-1a as an active ingredient, disaccharide as a bulking agent and a non-ionic surfactant such as polysorbate or PEG, and lyophilising the aqueous solution. Lyophilizers, which perform the above described lyophilization, are commercially available and readily operable by those skilled in the art. The lyophilisation process comprises typically three stages: freezing, primary drying and secondary drying, as described more detailed in the experimental part. Typically, an aqueous solution is lyophilised in vials, wherein each vials containing a unit dose of the interferon beta-1a formulation of the present invention. Consequently, a lyophilisate within a vial is a single dosage form according to the invention. The present formulation according to invention provides the formation of the soluble aggregate during freeze-drying.

Vessels, such as vials, containing a lyophilized formulation are preferably made of sterilisable and inert material. Suitable materials are e.g. polypropylene, cyclic olefin copolymers, standard glass type I and siliconized glass type I. Preferably, siliconized glass type I vials are used as packing material for avoiding the initial loss of Interferon beta-1a. The absorption of INF-beta 1a may be prevented through siliconization of an inner surface of the glass surface. According to a preferred embodiment of the invention an inner surface of the vessel, such as vial, is siliconized to avoid the initial loss of INF-beta 1a after freeze-drying. Use of polysorbate as a surfactant may also protect the protein against adsorption onto siliconized glass surfaces.

Before a lyophilisate can be administered to a patient it should be reconstituted with an aqueous reconstituent. This step permits interferon beta-1a and other components in the lyophilisate to re-dissolve to give an aqueous pharmaceutical composition which is suitable for intravenous injection to a patient. Typically, water for injection is used to reconstitute the lyophilisates. Typically, the volume of the reconstituted aqueous composition is between 0.9 to 1.1 mL, preferably 1 mL.

The interferon beta-1a is present at a concentration of 2 µg/mL to 15 µg/mL in the reconstituted aqueous composition. The reconstituted aqueous composition according to one embodiment of the invention further comprises
- 0.5-1.0 mg/mL, preferably 0.6-0.8 mg/mL of polysorbate or PEG as a surfactant,
- 30-50 mg/mL, preferably 35-40 mg/mL of trehalose or sucrose as a bulking agent,
- 15 to 28 mg/mL, preferably 18 to 22 mg/mL of a combination of buffering agents, which combination comprises disodium phosphate dihydrate, sodium dihydrogen phosphate dihydrate and trisodium citrate dihydrate, and
- 0.1-0.3 mg/mL, preferably 0.17 to 0.23 mg/mL of methionine as an antioxidant, and the pH of said aqueous composition is between 5.5 and 7.5, preferably between 6.0 and 7.0.

Where the interferon beta-1a formulation is used for delivery to a human, the isotonicity of the aqueous solution is also a consideration. Thus, in one embodiment of the invention, the aqueous solution for intravenous administration will provide isotonicity the same as, or similar, to that of patient serum or body fluids. The osmolality of reconstituted aqueous composition may be in the range of 250 to 350 mOsmol/kg.

An aqueous pharmaceutical composition of the invention can be administered into a patient. According to a preferred embodiment of the invention the aqueous pharmaceutical composition is suitable for intravenous administration. Administration will typically be via a syringe. Thus the invention also provides a delivery device and pre-filled syringe including an aqueous pharmaceutical composition of the invention. According to a preferred embodiment of the invention an inner surface of the delivery device or the pre-filled syringe is siliconized for preventing absorption of INF-beta 1a to the surface of the delivery device or pre-filled syringe and thus the invention provides a precise dosing of interferon beta-1a when administered intravenous into a patient. Suitable materials are same as previous mentioned as the material of vials. Typically, the lyophilisates were reconstituted using a 1 mL syringe. A precise dosage of the interferon beta-1a into the patent may be achieved by using the combination of the formulation according to the invention and the siliconized delivery device or syringe. The observed loss of interferon beta-1a during the reconstitution and delivering into the patient is only about 1 µg/dose, preferably below 1 µg/dose. Consequently, the invention provides a method for administering interferon beta-1a into the patient in such a manner that a loss of the interferon beta-1a is at most 1 µg/dose.

Patients will receive an effective amount of the interferon beta-1a as the principal active ingredient i.e. an amount that is sufficient to treat, ameliorate, or prevent the disease or disorder in question. The optimum effective amount and concentration of interferon beta-1a for any particular subject will depend upon various factors, including the patient's age, size, health and/or gender, the nature and extent of the condition, and also on any possible further therapeutic(s) administered in combination with the interferon beta-1a. The effective amount delivered for a given situation may be determined with in the judgment of a clinician. For purposes of the present invention, interferon beta-1a may be administrated into the patient (age ≥18 years) at 7.5-12.5 µg/dose for prevention and/or treatment of vascular-endothelial diseases in adult patients with intravenous administration. If a patient is less than 18 years in age, interferon beta-1a may be administrated at 2.0-12.5 µg/dose for prevention and/or treatment of vascular-endothelial diseases in patients with intravenous administration. Consequently, the invention also concerns a method for delivering a pharmacologically effective amount of interferon beta-1a to a patient comprising a step of administering to the patient an aqueous pharmaceutical composition of the invention. The invention also concerns use of delivery device or pre-filled syringe in administration of interferon beta in a patient at precise dose.

The formulation of the invention may be used to treat a range of vascular-endothelial diseases in humans. The CD73, an endothelial ectoenzyme, which can produce local adenosine, is a key molecule to maintain endothelial barrier and lung function. Interferon-beta increases CD73 expression resulting in increased local adenosine. Many inflammatory conditions are known to result in the loss of CD73 from the surfaces of inflamed/injured endothelial cells, therefore reducing available adenosine content. The anti-inflammatory properties of adenosine are well known in the literature and any condition that is known to result from the loss of local adenosine effect will benefit from the up-regulation of CD73 expression. If permanent help is needed, the up-regulation of CD73 should be based on de novo synthesis.

Consequently, a lyophilised formulation or an aqueous pharmaceutical composition according to the invention is suitable for prevention and/or treatment of vascular-endothelial diseases in humans. More specifically, a lyophilised formulation or an aqueous pharmaceutical composition according to the invention is suitable for prevention and/or treatment of vascular-endothelial diseases in patients with intravenous administration, wherein interferon beta-1a is administrated into the patient at 7.5-12.5 µg/dose, or at 2.0-12.5 µg/dose, if the patient is less than 18 years in age.

According to an embodiment of the invention a lyophilised formulation or an aqueous pharmaceutical composition according to the invention is suitable for use in the prevention and/or treatment vascular leakage in acute respiratory distress syndrome (ARDS), systemic inflammatory response syndrome (SIRS) and other traumatic conditions.

According to another embodiment of the invention a lyophilised formulation or an aqueous pharmaceutical composition according to the invention is suitable for use in the prevention and/or treatment of ischemia-reperfusion injury in vascular or cardiac surgery and organ transplantation, or for use in ischemic pre-conditioning prior to major vascular or cardiac surgery and organ transplantation. In addition, a lyophilised formulation or an aqueous pharmaceutical composition according to the invention is suitable for use in the prevention and/or treatment of ischemia-reperfusion injury in myocardial infarction and stroke.

According to another embodiment of the invention a lyophilised formulation or an aqueous pharmaceutical composition according to the invention is suitable for use in the prevention and/or treatment of acute pancreatitis and acute kidney injury, but not limited these examples.

According to another embodiment of the invention a lyophilised formulation or an aqueous pharmaceutical composition according to the invention is suitable for use in severe life threatening viral infections such as EBOLA, MERS, influenza such as avian flu, and other similar conditions leading to a systemic inflammatory response syndrome (SIRS) and dysfunction of central organs.

According to another embodiment of the invention a lyophilised formulation or an aqueous pharmaceutical composition according to the invention is suitable for use in severe bacterial pneumonia and sepsis leading to a systemic inflammatory response syndrome (SIRS) and multi-organ failure (MOF), or for use in the prevention and/or treatment of MOF.

A method of treating a patient comprises at least the following steps
  providing a lyophilized formulation according to the invention,
  reconstituting the lyophilized formulation, and
  administering the reconstituted aqueous composition to a patient.

In one of the embodiments of the method of treating a patient described herein, the patient has vascular-endothelial disease. The administration of IFN-beta 1a should start as early as possible after disease diagnosis and should continue a minimum of six days with daily administration of the desired dose.

The following examples are offered by way of illustration and not by way of limitation.

EXPERIMENTAL PART

The invention is described in more detailed in the following experiments. The experimental part of the present application is divided to different parts. The first part, "Formulation study A", is focused on to compare different excipients for stabilization of INF-beta 1 a. The stability studies dealt with the composition of the lyo solution to ensure a stability of INF-beta 1a for 4 weeks at 40° C. in the freeze dried state. The second part, "Formulation study B", based on the results of the formulation study A, and the selected formulations were included in a further study for determining the effective ratio of the excipients. The third part, "Freeze drying study", is focused on a lyo cycle suitable for the formulations according to the present invention. The forth part, "stability study", investigate the compatibility of lyophilised formulation according to the invention with device and prefilled WFI syringe used in reconstitution and clinical application. The fifth part, "Bio-efficacy study", determines the efficacy of lyophilised product of interferon beta-1a.

1. Formulation Study A

The different formulations were analyzed with regard to the recovery of interferon beta-1a after reconstitution and the formation of soluble aggregates during freeze-drying. Formulations were composed based on a feasibility study. In addition, samples were stored at 40° C. over 12 weeks and the content of Interferon beta-1a was analyzed at fixed time points to identify the most stable formulations during storage.

Formulation of the INF Beta-1a Lyophilisation Solution

The INF beta-1a drug substance (provided by Rentschler Biotechnologie GmbH) was purified to remove existent insoluble aggregates via centrifugation (10 min, 4000 rpm) and sterile filtration (0.2 µm) before compounding was started. The resulting Interferon beta-1a concentration was measured by UV spectroscopy (280 nm; UV-spectrometer Carry 50, Varian), yielded 285 µg/ml after three different purification procedures. The calculation of the INF beta-1a concentration was based on the extinction coefficient (1.351 mL*µg$^{-1}$*cm$^{-1}$).

The excipients were added to the citrate buffer used as liquid formulation according to the corresponding target concentration. Table 1 lists different formulations which were utilized. Bulking agents were selected from the chemical classes of disaccharides, amino acids, and sugar alcohols and two of them (sucrose and mannitol) were additionally combined. All excipients were additionally combined with Tween 20. These stock solutions were mixed with the purified INF beta-1a drug substance in a ratio to achieve an INF-beta 1a concentration of 30 µg/ml.

TABLE 1

Different formulations of INF beta-1a lyo solution. The values are % (w/v) of the lyo-solution.

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Sucrose | 5 | | | | | | 2.5 | 5 | | | | | | 2.5 |
| Trehalose | | 5 | | | | | | | 5 | | | | | |
| Arginine phosphate | | | 5 | | | | | | | 5 | | | | |
| Glycine | | | | 5 | | | | | | | 5 | | | |
| Mannitol | | | | | 5 | | 2.5 | | | | | 5 | | 2.5 |
| Polysorbate 20 | | | | | | | | 0.1 | 0.1 | 0.1 | 0.1 | 0.1 | 0.1 | 0.1 |

After sterile filtration, 1 ml of the corresponding lyo-solution was filled into 10R glass type I vials.

Lyophilization

The filled vials were loaded into the freeze dryer and shielded against thermal radiation. The freeze-drying cycle listed in Table 2 was used for the preparation of the samples.

TABLE 2

Steps of the freeze-drying cycle used to manufacture the samples for the feasibility study and the stability study

| | Shelf temperature [° C.] | Time/ Step [hh]:[mm] | Total elapsed time [hh]:[mm][ss] | Pressure [mbar] | Total elapsed time [hours] |
|---|---|---|---|---|---|
| Start | 5 | 00:00 | 0:00:00 | 1000 | 0.00 |
| 1 Incubation | 5 | 00:10 | 0:10:00 | 1000 | 0.17 |
| 2 Freezing (ramp) | −40 | 00:30 | 0:40:00 | 1000 | 0.67 |
| 3 Freezing | −40 | 03:00 | 3:40:00 | 1000 | 3.67 |
| 4 Therm. treatment (ramp) | −10 | 00:30 | 4:10:00 | 1000 | 4.17 |
| 5 Therm. treatment | −10 | 04:00 | 8:10:00 | 1000 | 8.17 |
| 6 Therm. treatment (ramp) | −40 | 00:30 | 8:40:00 | 1000 | 8.67 |
| 7 Freezing | −40 | 03:00 | 11:40:00 | 1000 | 11.67 |
| 8 Vacuum adj. | −40 | 00:30 | 12:10:00 | 0.1 | 12.17 |
| 9 Prim. drying (ramp) | −20 | 02:00 | 14:10:00 | 0.1 | 14.17 |
| 10 Prim. drying | −20 | 34:00:00 | 48:10:00 | 0.1 | 48.17 |
| 11 Sec. drying (ramp) | 25 | 08:00 | 56:10:00 | 0.1 | 56.17 |
| 12 Sec. drying | 25 | 10:00 | 66:10:00 | 0.1 | 66.17 |
| 13 Venting N2 | 25 | 00:10 | 66:20:00 | 1000 | 66.33 |
| Total | | | 66:20:00 | | 66.33 |

Reconstitution of Lyophilisates 1 ml WFI (water for injection) was added to the lyophilisates to reconstitute them. After complete dissolution, the solution was homogenized by pipetting three times up and down and transferred into a reaction tube. The content of Interferon beta-1a was analyzed after reconstruction using RP-HPLC method according to manufacturer's operating procedures.

TABLE 3

Amount of INF-beta 1a per vial after reconstitution; target amount was 30 μg/vial.

| Formulation | INF-β1a amount per vial |
|---|---|
| 5% sucrose | 7.2 ± 0.1 |
| 5% trehalose | 6.7 ± 0.4 |
| 5% arginine phosphate | 8.8 ± 2.6 |
| 5% glycine | 11.0 ± 0.3 |
| 5% mannitol | 19.6 ± 0.9 |
| 2.5% sucrose + 2.5% mannitol | 7.2 ± 0.2 |
| 5% sucrose + 0.1% Tween 20 | 30.0 ± 0.3 |
| 5% trehalose + 0.1% Tween 20 | 31.0 ± 0.1 |
| 5% arginine phosphate + 0.1% Tween 20 | 30.5 ± 0.1 |
| 5% glycine + 0.1% Tween 20 | 30.8 ± 0.0 |
| 5% mannitol + 0.1% Tween 20 | 30.7 ± 0.0 |
| 2.5% sucrose + 2.5% mannitol + 0.1% Tween 20 | 31.7 ± 0.1 |

All formulations without Tween 20 yielded only a marginal recovery of the applied INF-beta 1a after reconstitution, only one third of the target amount. Formulations containing Tween 20 showed a completely opposed picture. The recovery after reconstitution yielded the target amount independent from the used excipient. Hence, it is obvious that detergents such as Tween 20 or the like, which achieve a spatial isolation of several INF-beta 1a molecules, are needed to prevent loss of INF-beta 1a during freeze-drying and reconstitution.

In parallel, a non-reducing SDS-PAGE method according to manufacturer's operating procedures was performed for the reconstituted lyophilisates. To achieve non-reducing conditions, the reducing agent was replaced by distilled water. The charge per well was kept constant at 6 μg. No quantification was performed. FIGS. 1 to 4 display the obtained gels. White numbers in the Figures mark the lines whereas black numbers indicate the molecular weight.

FIG. 1: Line 1+9: MW-marker; Line 2+3: 5% sucrose; Line 4+5: 5% trehalose; Line 6+7: 5% arginine phosphate; Line 8: drug substance; Line 10: reference material.

FIG. 2: Line 1+2: 5% glycine; Line 3+9: MW-marker; Line 4+5: 5% mannitol; Line 6+7: 2.5% sucrose+2.5% mannitol; Line 8: drug substance; Line 10: reference material.

Figures 3, 4:
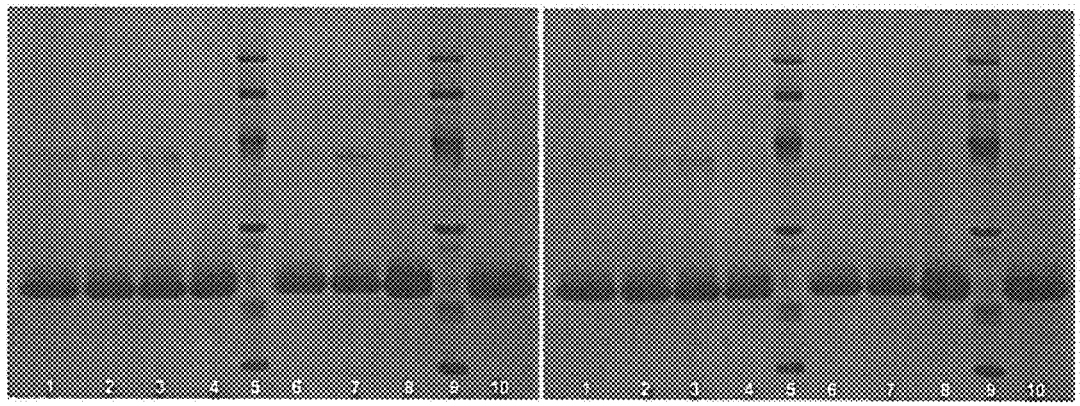

FIG. 3: Line 1+2: 5% sucrose+0.1% Tween 20; Line 3+4: 5% trehalose+0.1% Tween 20; Line 5+9: MW-marker; Line 6+7: 5% arginine phosphate+0.1% Tween 20; Line 8: drug substance; Line 10: reference material.

FIG. 4: Line 1+6: MW-marker; Line 2+3: 5% glycine+0.1% Tween 20; Line 4+5: 5% mannitol+0.1% Tween 20; Line 7+8: 2.5% sucrose+2.5% mannitol+0.1% Tween 20; Line 9: drug substance; Line 10: reference material.

Gel one (see FIG. 1) and gel two (FIG. 2) were loaded with the formulations lacking Tween 20. The band intensity of the individual samples differs due to the varying recovery of INF-beta 1a (see Table 3). The formulations on gel one (sucrose, trehalose and arginine phosphate) show a weak band, which exhibits the molecular weight of dimeric INF-beta 1 a, aside from the INF-beta 1a main band. This band also appeared in the drug substance (see line 8 in FIG. 1). Hence, no soluble aggregates were further generated in the presence of these excipients during freeze drying. A similar picture was seen on gel two. The formulations with glycine and a mixture of sucrose and mannitol exhibit only marginal dimeric bands (see line 1+2 and 6+7 in FIG. 2). However, that could be ascribed to the low protein load in these lines due to poor INF-beta 1a recovery. The mannitol formulation showed a dimeric band. Its intensity is comparable to that of the drug substance (see line 4+5 in FIG. 2). Hence, no soluble aggregates were further generated in the presence of these excipients during freeze-drying either.

Gel three (see FIG. 3) and gel four (see FIG. 4) were loaded with formulations containing Tween 20. The band intensity of all samples is constant due to the complete recovery of INF-beta 1a. All formulations on gel three and gel four exhibit dimeric bands whose intensity is comparable to the dimeric band of the drug substance. No soluble aggregates were generated in these formulations during freeze drying either.

Stability of Lyophilisates

The formulations listed in Table 4 were prepared based on the results of the freeze-drying feasibility study above using the same freeze-drying cycle as before (described in Table 2).

TABLE 4

Different formulations manufactured for the first stability study. The values are % (w/v) of the lyo-solution.

| | 1 | 2 | 3 | 4 | 5 | 6 | 7 | 8 | 9 | 10 |
|---|---|---|---|---|---|---|---|---|---|---|
| Sucrose | 5 | | | | | 2 | 2.5 | 1 | | 2.5 |
| Trehalose | | 5 | | | | | | | | |
| Arginine phosphate | | | 5 | | | | | 4 | 5 | |
| Glycine | | | | 5 | | | | | | |
| Mannitol | | | | | 5 | 2 | 2.5 | | | 2.5 |
| Tween 20 | 0.1 | 0.1 | 0.1 | 0.1 | 0.1 | | 0.1 | 0.1 | | |
| Tween 80 | | | | | | | | | 0.1 | 0.1 |

Sucrose and trehalose represent the class of disaccharides, arginine phosphate and glycine are commonly used amino acids and mannitol is an often applied excipient from the class of sugar alcohols. Substances from these chemical groups are able to stabilize proteins inside the lyo-cake through hydrogen bonds. All formulations contained either Tween 20 or Tween 80. The concentration of methionine, which is also present in the liquid formulation of INF-beta 1a, was kept constant to sustain protection against oxidation.

RP-HPLC Analysis of INF-Beta 1a During Stability Study at 40° C.

The methods RP-HPLC and SDS-PAGE were applied for the analysis of INF-beta 1a during the stability study. The RP-HPLC method permits the quantification of INF-beta 1a as well as the determination of degradation products including oxidation products, aggregation products and changes in protein folding. Samples were analyzed after freeze drying and a storage period of 2 weeks, 4 weeks, 8 weeks and 12 weeks at 40° C.

Figure 5:
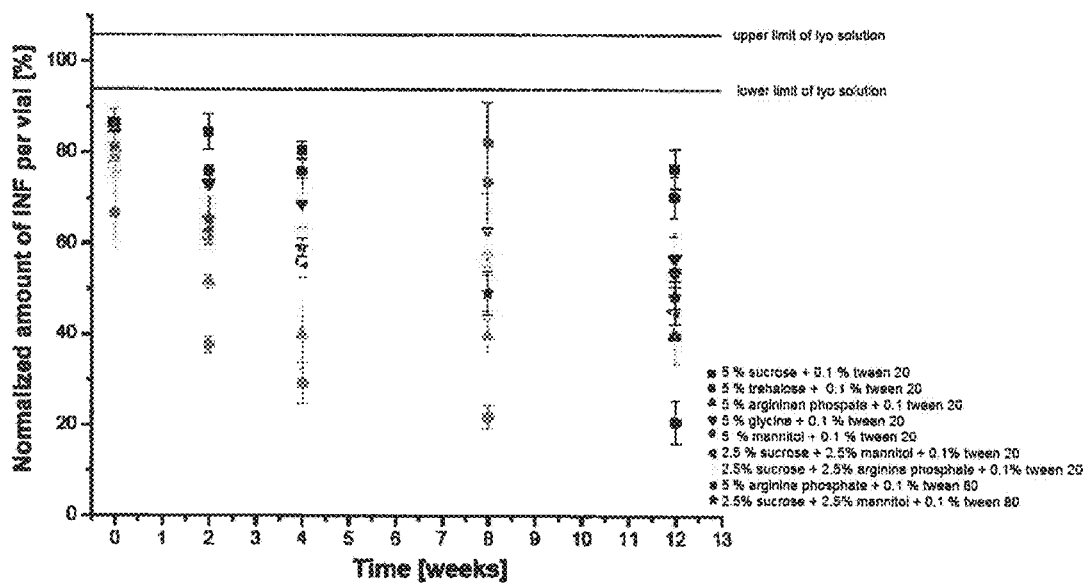
FIG. 5 shows the quantification of INF-beta 1a after reconstitution of the lyophilisates. See Formulation study A of the experimental part.

FIG. 5 shows the quantification of INF-beta 1a after reconstitution of the lyophilisates. The quantification was performed based on the total peak area including degradation products. Black lines mark the upper and lower value of the lyo-solution before freeze-drying representing the 100% limit.

The resolvable INF-beta 1a content of most formulations ranged around 80% recovery (loss of 6 µg), directly after freeze-drying. Best recovery was obtained with the sucrose/Tween 20 and the sucrose/mannitol/Tween 80 formulations (about 90% recovery). The duster of formulations including trehalose/Tween 20, arginine phosphate/Tween 20, glycine/Tween 20 and mannitol/Tween 20 along with the sucrose/mannitol/Tween 20 formulation yielded the second best recovery with a value of about 80%. The worst recovery (less than 70%) was obtained with the arginine phosphate/Tween 80 and sucrose/arginine phosphate/Tween 20 formulations.

After storage at 40° C. for 1 week, the recovery of the individual formulations began to differ significantly. The recovery of the sucrose/Tween 20 formulation remained constant at 90%. Trehalose/Tween 20 and glycine/Tween 20 also showed recovery values comparable to their starting point. The recovery of all other formulations decreased more or less. Major loss was observed for the arginine phosphate/Tween 20 (about 50%) and arginine phosphate/Tween 80 (less than 40%) formulation. All other formulations ranged at a recovery of about 65%.

The picture remained nearly constant after 2 weeks storage. Again, the sucrose/Tween 20 and the trehalose/Tween 20 formulation showed constant recovery only that now the recovery of the glycine/Tween 20 formulation began to decrease (about 5% in comparison to the previous time point). The recovery of all other formulations dropped about 10%.

After storage at 40° C. for 12 weeks, the sucrose/Tween 20 and the trehalose/Tween 20 formulations clearly showed the best recovery at a still constant value. So, no loss of active agent was observed in these formulations during storage over a time period of 12 weeks at 40° C. All other formulations exhibited a greater or lesser decrease of recovered INF-beta 1a.

Figure 6:
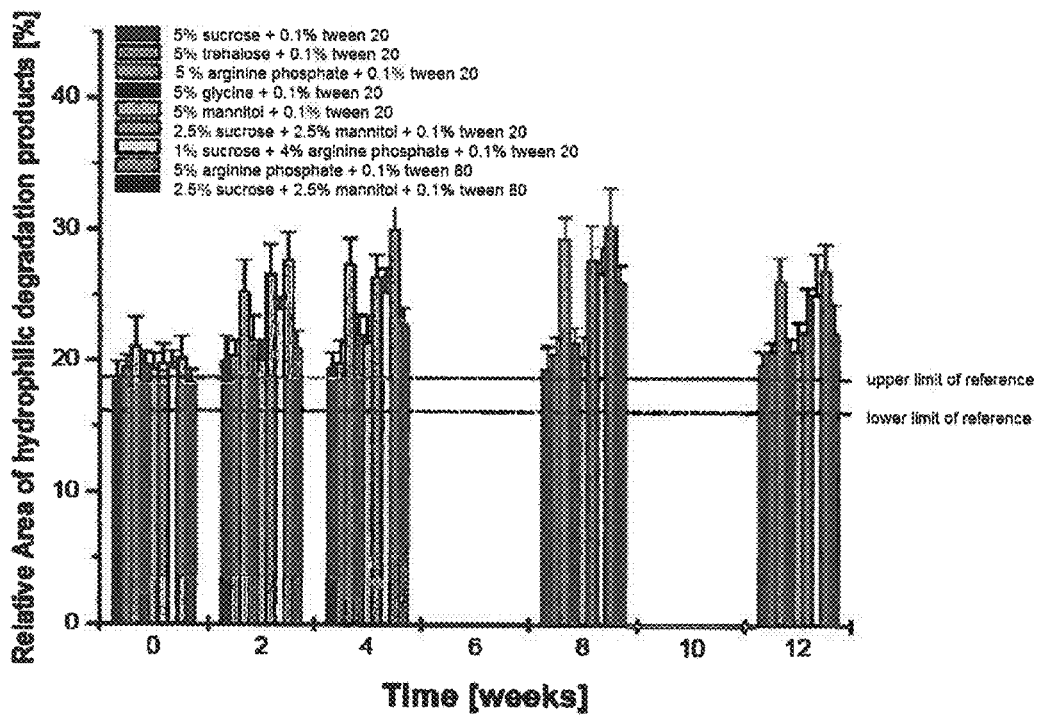
FIG. 6 shows the progress of the relative peak area of hydrophilic peaks representing the increase of oxidized INF-beta 1a species during storage at 40° C. during stability study of the formulation study A.

FIG. 6 shows the progress of the relative peak area of hydrophilic peaks representing the increase of oxidized INF-beta 1a species during storage at 40° C. Black lines mark the upper and the lower limit of the relative peak area of hydrophilic peaks from the reference material chromatogram.

At the level of the reference material, the relative peak area of oxidized INF-beta 1a remained constant in all formulations directly after freeze-drying. Hence, the freeze-drying manufacturing step did not induce INF-beta 1a oxidation.

During storage, the relative peak area of these degradation products increases more or less depending on the present excipient. After storage at 40° C. for 2 weeks, the arginine phosphate/Tween 20, sucrose/mannitol/Tween 20, arginine phosphate/Tween 80 and the sucrose/arginine phosphate/Tween 20 formulations showed a clear increase of the relative peak area (about 8%). The relative hydrophilic peak area of the other formulations remained constant. After a storage period of 2 weeks, no further increase of the relative peak area of oxidized species was observed in any of the formulations except for the sucrose/mannitol/Tween 80 formulation, which showed a steady increase of the relative peak area of the hydrophilic degradation products up to 8 weeks of storage at 40° C. This picture prevailed until the time point of 12 weeks was reached. Hence it can be assumed that the formulations with sucrose/Tween 20, trehalose/Tween 20, glycine/Tween 20 and mannitol/Tween 20 are able to protect INF-beta 1a against oxidation up to a storage period of 12 weeks at 40° C. Additionally the main stabilizing effect against oxidation is ascribed to present methionine. But since all formulations contained the same amount of methionine, some excipients seem to add to the stabilizing effect of methionine.

Figure 7:
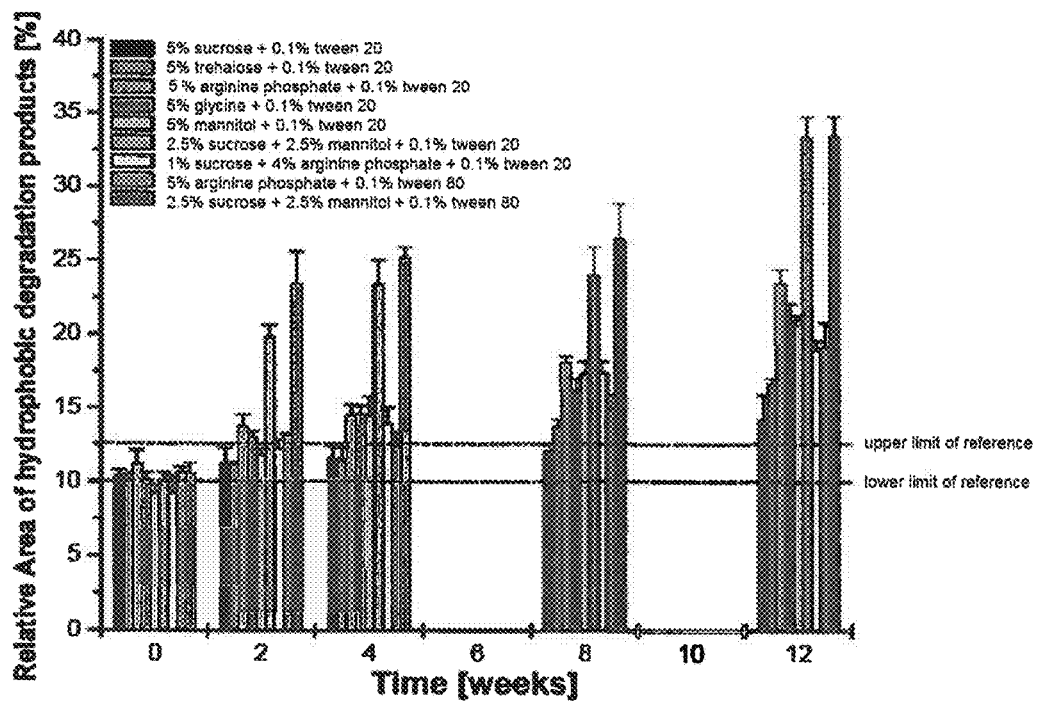
FIG. 7 shows the progress of the relative peak area of hydrophobic peaks representing the increase of INF-beta 1a species which indicate a change in protein folding during storage at 40° C. See formulation study A of the experimental part.

FIG. 7 shows the progress of the relative peak area of hydrophobic peaks representing the increase of INF-beta 1a species which indicate a change in protein folding during storage at 40° C. Black lines mark the upper and lower limit of the relative peak area of hydrophobic peaks from the reference material chromatogram.

Only hydrophobic degradation products were observed during the stability study, which can be ascribed to INF-beta 1a species with an altered folding state. No formation of soluble aggregates was observed in any of the samples. Hence, it is not the aggregation of INF-beta 1a representing the problem. None of the formulations showed any increase of hydrophobic degradation products directly after lyophilization. Hence, freeze-drying alone did not cause a change in INF-beta 1a folding. The two formulations with sucrose/Tween 20 and trehalose/Tween 20 exhibited the best stabilizing effect against such degradation products during storage. All other formulations showed a greater or lesser increase of these degradation products throughout the 12 week stability study. A considerable increase of hydrophobic degradation products was seen in the sucrose/mannitol/Tween and sucrose/mannitol/Tween 80 formulations.

RP-HPLC analyses revealed that sucrose and trehalose are the most suitable excipients for the stabilization of INF-beta 1a in the freeze-dried state.

SDS-PAGE Analysis of INF-Beta 1a During the Stability Study at 40° C.

The gels obtained with SDS-PAGE at each time point of the stability study. Non-reduced conditions were maintained at all time points whereas reduced conditions were only applied at the time points of 8 weeks and 12 weeks. After 8 weeks, the formulations with arginine phosphate/Tween 20 and arginine phosphate/Tween 80 were not analyzed because the recovery of these formulations was not satisfying as indicated by RP-HPLC measurements.

No changes occurred in the band pattern in any of the samples when compared to the INF-beta 1a drug substance or the reference material neither directly after lyophilisation nor within the first 4 weeks of storage. Some samples showed a weaker dimeric band on one gel than on the next gel, but no tendency for increasing dimeric band intensity was seen with ongoing storage duration. After storage at 40° C. for 8 weeks, the formulations mannitol/Tween 20, sucrose/mannitol/Tween 20, sucrose/arginine phosphate/Tween 20 and sucrose/mannitol/Tween 80 showed an increase in the dimeric band under non-reducing conditions. All other formulations showed no changes in their band patterns. After storage for 12 weeks at 40° C., no further changes in the peak pattern were observed in any of the formulations when compared to the peak patterns after storage at 40° C. for 8 weeks.

Figures 8, 9:
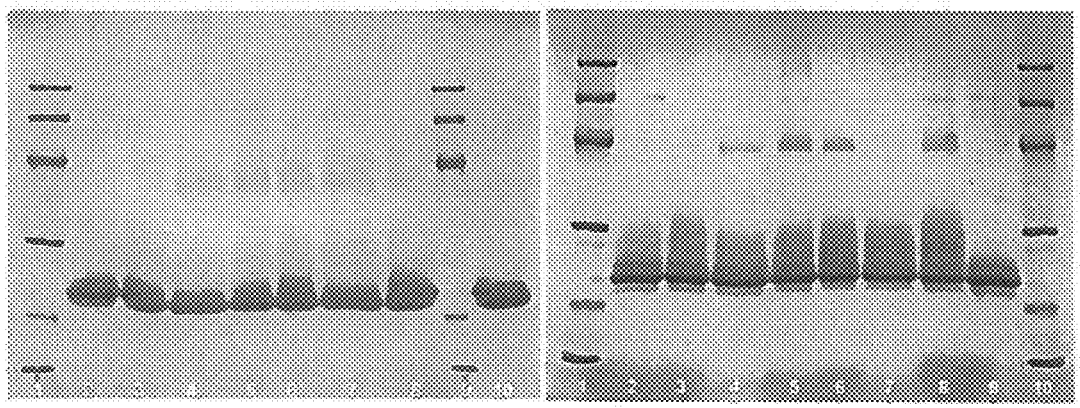
FIG. 8 shows Non-reducing SDS-PAGE of reconstituted lyophilisates of formulations after storage at 40° C. for 12 weeks. See formulation study A.
FIG. 9 shows Reducing SDS-PAGE of reconstituted lyophilisates of formulations after storage at 40° C. for 1.2 weeks. See formulation study A.

FIG. 8 shows Non-reducing SDS-PAGE of reconstituted lyophilisates of formulations 1, 2, 4, 5, 7, 8 and 9 of Table 4 after storage at 40° C. for 12 weeks. White numbers mark the lines whereas black numbers indicate the molecular weight. Line 1+9: MW-marker; Line 2: 5% sucrose+0.1% Tween 20; Line 3: 5% trehalose+0.1% Tween 20; Line 4: Line 5: 5% glycine+0.1% Tween 20; Line 5: 5% mannitol+1% Tween 20; Line 6: 2.5% sucrose+2.5% mannitol+0.1% Tween 20; Line 7: 1% sucrose+4% arginine phosphate+0.1% Tween 20; Line 8: 2.5% sucrose+2.5% mannitol+0.1% Tween 80; Line 10: drug substance.

FIG. 9 shows Reducing SDS-PAGE of reconstituted lyophilisates of formulations 1, 2, 4, 5, 7, 8 and 10 of Table 4 after storage at 40° C. for 12 weeks. White numbers mark the lines whereas black numbers indicate the molecular weight. Line 1+10: MW-marker; Line 2: 5% sucrose+0.1% Tween 20; Line 3: 5% trehalose+0.1% Tween 20; Line 4: Line 5: 5% glycine+0.1% Tween 20; Line 5: 5% mannitol+1% Tween 20; Line 6: 2.5% sucrose+2.5% mannitol+0.1% Tween 20; Line 7: 1% sucrose+4% arginine phosphate+0.1% Tween 20; Line 8: 2.5% sucrose+2.5% mannitol+0.1% Tween 80; Line 9: drug substance.

All in all SDS-PAGE results showed that most stable peak patterns of INF-beta 1a were obtained with the trehalose/Tween 20 and the sucrose/Tween 20 formulation.

Absorption onto Glass Surfaces

Figure 10:
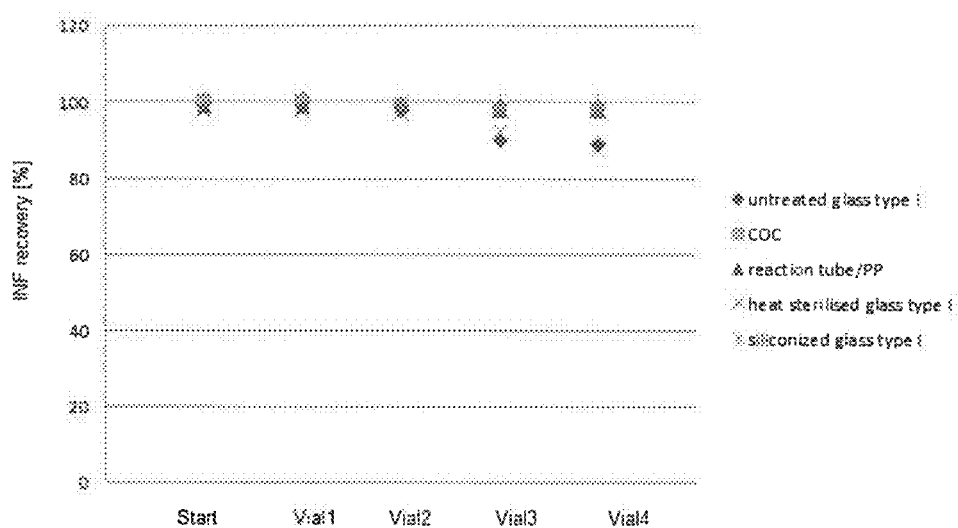
FIG. 10 shows loss of INF-beta 1a due to adsorption onto surfaces of different materials. See the last part of the formulation study A.

The experiment was aimed at investigating the amount of adsorption of INF-beta 1a in its liquid state onto surfaces of different materials. The choice of vial materials used as primary packaging material for freeze-dried products is limited because the material must be sterilizable and inert. Based on these prerequisites, the following materials are suitable: polypropylene (PP), cyclic olefine copolymers (COC), standard glass type 1 and siliconized glass type 1. In some cases, heat treatment of glass type 1 also shows an influence on the adsorption behaviour of proteins onto the surface. Therefore, untreated glass vials and heat sterilized glass vials were used in the next experiment. The amount of adsorption was measured in the presence of Tween only. Results are illustrated in FIG. 10.

The recovery of the samples filled into COC vials, PP vials as well as siliconized glass type 1 vials remained constant up to the fourth container change. Samples filled into untreated and heat sterilized glass type 1 vials exhibited a decrease in recovery of about 10% (see FIG. 10). This experiment clearly demonstrates that the adsorption of INF-beta 1a could be eliminated with more hydrophobic surfaces in the presence of Tween. Hence, it is recommended to use siliconized glass type 1 vials as primary packaging material.

2. Formulation Study B

This formulation study is based on the results of the formulation study A and the selected formulations were included in a further study for determining the effective ratio of the excipients.

Compounding of the INF-Beta 1a Lyo Solution

The INF-beta 1a drug substance (provided by Rentschler Biotechnologie GmbH) was purified via centrifugation (10 min, 4000 rpm) and sterile filtration (0.2 µm) to remove existent insoluble aggregates before compounding was started. The resulting INF-beta 1a concentration was measured by UV spectroscopy (280 nm; UV spectrometer Carry 50, Varian). The calculation of the INF-beta 1a concentration was based on the extinction coefficient (1.351 mL* $\mu g^{-1}$*$cm^{-1}$).

The excipients as well as the buffer components were dissolved in WFI (water for injection) in the corresponding ratio. Different formulations of the study B are listed in Table 5. The exact content of one vial of each formulation is listed in Table 6. Purified INF-beta 1a drug substance was added to achieve an INF-beta 1a concentration of approximately 24 µg/mL in the final lyo solution. Finally the different lyo solutions were filled up with WFI to the target weight, which was calculated based on the density of the lyo solutions.

TABLE 5

Different formulations for study B.
The values represent % (w/v) of the lyo solution.

|  | 1 | 2 | 3 | 4 |
| --- | --- | --- | --- | --- |
| Sucrose | 5 |  | 7.5 |  |
| Trehalose |  | 5 |  | 7.5 |
| Methionine | 0.03 | 0.03 | 0.03 | 0.03 |
| Tween 20 | 0.1 | 0.1 | 0.1 | 0.1 |

TABLE 6

Exact content of one vial of each formulation in mg.

| | Amount per Vial [mg] | | | |
| --- | --- | --- | --- | --- |
| Variant | 1 | 2 | 3 | 4 |
| Sucrose | 50 | 0 | 75 | 0 |
| Trehalose | 0 | 50 | 0 | 75 |
| Methionine | 0.3 | 0.3 | 0.3 | 0.3 |
| Tween 20 | 1 | 1 | 1 | 1 |
| Sodium citrate | 18 | 18 | 18 | 18 |
| Sodium phosphate | 8.2 | 8.2 | 8.2 | 8.2 |
| INF-β1a | 0.024 | 0.024 | 0.024 | 0.024 |
| Sum | 76.52 | 76.52 | 101.5 | 101.5 |

After sterile filtration, 1 mL of the corresponding lyo solution was filled into siliconized 10R glass type 1 vials.

The density of the lyo solutions containing 5% sucrose and 5% trehalose was 1.034 g/ml at 25° C. whereas the measured density of the lyo solutions containing 7.5% sucrose and 7.5% trehalose was 1.043 g/ml at 25° C.

Lyophilization

The filled vials were loaded into the freeze dryer and shielded against thermal radiation. The freeze drying cycle listed in Table 7 was used for the preparation of the samples.

TABLE 7

Steps of the freeze drying cycle used.

|   | | Shelf temperature [° C.] | Time/ Step [hh]:[min] | Total elapsed time [hh]:[min] | Pressure [mbar] | Total elapsed time [hh]:[mm] |
|---|---|---|---|---|---|---|
|   | Start | 5 | 00:00 | 0:00:00 | 1000 | 0.00 |
| 1 | Incubation | 5 | 00:10 | 0:10:00 | 1000 | 0.17 |
| 2 | Freezing (ramp) | −40 | 00:30 | 0:40:00 | 1000 | 0.67 |
| 3 | Freezing | −40 | 03:00 | 3:40:00 | 1000 | 3.67 |
| 4 | Vacuum adj. | −40 | 00:30 | 4:10:00 | 0.1 | 4.17 |
| 5 | Prim. drying (ramp) | −20 | 02:00 | 6:10:00 | 0.1 | 6.17 |
| 6 | Prim. drying | −20 | 34:00:00 | 40:10:00 | 0.1 | 40.17 |
| 7 | Sec. drying (ramp) | 35 | 10:00 | 50:10:00 | 0.1 | 50.17 |
| 8 | Sec. drying | 35 | 10:00 | 60:10:00 | 0.1 | 60.17 |
| 9 | Venting N2 | 35 | 00:10 | 60:20:00 | 1000 | 60.33 |
|   | Total | | | 60:20:00 | | 60.33 |

All obtained lyophilisates showed a good macroscopic appearance without any defects or collapse.

Reconstitution of Lyophilisates 1 ml WFI was added to the lyophilisates to reconstitute them. After complete dissolution, the solution was homogenized by pipetting three times up and down and transferred into a HPLC vial. INF-beta 1a content was determined using RP-HPLC. The RP-HPLC method was performed according to according to manufacturer's operating procedures.

INF-Beta 1a Content of the Lyo Solutions and Lyophilisates

The INF-beta 1a content of the lyo solutions and the reconstituted lyophilisates was measured using RP-HPLC directly after lyophilization. Table 8 shows the INF-beta 1a content of the lyo solutions.

TABLE 8

INF-beta 1a content of the lyo solutions; target content was 24 μg/ml.

| # | Formulation | INF-β1a content [μg/ml] |
|---|---|---|
| 1 | 5% Sucrose + 0.1% Tween 20 | 25.9 ± 1.3 |
| 2 | 5% Trehalose + 0.1% Tween 20 | 26.1 ± 0.7 |
| 3 | 7.5% Sucrose + 0.1% Tween 20 | 26.3 ± 0.5 |
| 4 | 7.5% Trehalose + 0.1% Tween 20 | 26.6 ± 0.5 |

The recovery of INF-beta 1a after reconstitution of the lyophilisates was determined directly after freeze drying. Results are listed in Table 9. All formulations showed complete recovery of INF-beta 1a within the standard deviation of the lyo solutions.

TABLE 9

Recovery of INF-beta 1a after reconstitution of the lyophilisates directly after freeze drying

| # | Formulation | Recovery of INF-β1a [%] |
|---|---|---|
| 1 | 5% Sucrose + 0.1% Tween 20 | 97.7 ± 3.5 |
| 2 | 5% Trehalose + 0.1% Tween 20 | 96.2 ± 1.9 |

TABLE 9-continued

Recovery of INF-beta 1a after reconstitution of the lyophilisates directly after freeze drying

| # | Formulation | Recovery of INF-β1a [%] |
|---|---|---|
| 3 | 7.5% Sucrose + 0.1% Tween 20 | 96.2 ± 2.3 |
| 4 | 7.5% Trehalose + 0.1% Tween 20 | 95.9 ± 1.9 |

Residual Water Content of the Lyophilisates

To promote optimal storage stability of the lyophilisates, the content of residual (here: only free, not bound) water of the lyo cakes was measured by Karl Fischer titration. The values for the content of free residual water, determined in the lyophilisates directly after freeze drying, are listed in Table 10. All formulations contained about 1% free residual water.

In Karl Fisher titration closed vials were transferred into the oven (80° C.) of the Karl Fischer coulometer where the injection needle penetrated the stopper. The water vapor generated at 80° C. was directly transferred over the injection needle into the titration chamber of the Karl Fischer coulometer using dry nitrogen. The calculation of the residual water content was based on the theoretical weight of the lyo cake.

TABLE 10

Free water content of the individual formulations after freeze drying.

| # | Formulation | Free water content [wt-%] |
|---|---|---|
| 1 | 5% Sucrose + 0.1% Tween 20 | 1.04 ± 0.14 |
| 2 | 5% Trehalose + 0.1% Tween 20 | 1.08 ± 0.12 |
| 3 | 7.5% Sucrose + 0.1% Tween 20 | 0.97 ± 0.06 |
| 4 | 7.5% Trehalose + 0.1% Tween 20 | 0.88 ± 0.05 |

Adsorption of INF-Beta 1a to Siliconized Glass Vials and to Stoppers

Two types of siliconized glass vials from different suppliers (Gerresheimer AG, Schott AG) were used for this study. The vials of both suppliers were tested with regard to the adsorption of INF-beta 1a from aqueous solution.

Figure 11:
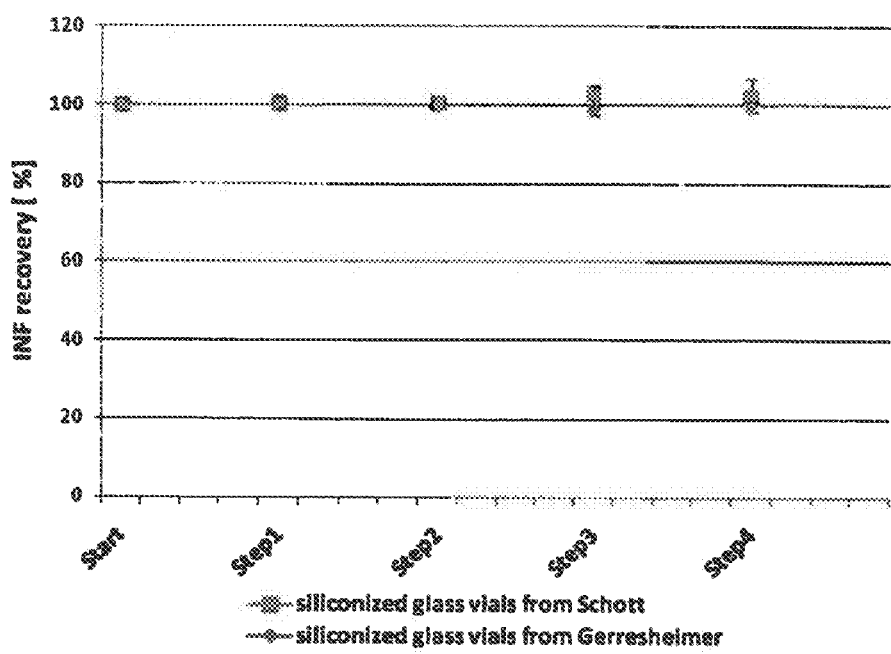
FIG. 11 shows recovery of INF-beta 1a during sample transfer from one vial to another. See formulation study B.

Purified INF-beta 1a DS was diluted to a concentration of 30 µg/ml with citrate buffer containing Tween 20. The Tween 20 concentration was set to 0.1% (w/v). The solution was filled into siliconized vials from different manufacturers. Samples were taken after short incubation and the remaining solution was transferred into a new vial of the corresponding type. This procedure was repeated four times. The INF-beta 1a content of the samples was analyzed using RP-HPLC. FIG. 11 shows the results of the study. The concentration of INF-beta 1a remains constant over all four transfer steps irrespective of the used vial. Hence, adsorption of INFbeta 1a to the glass surface can be neglected in both cases.

Figure 12:
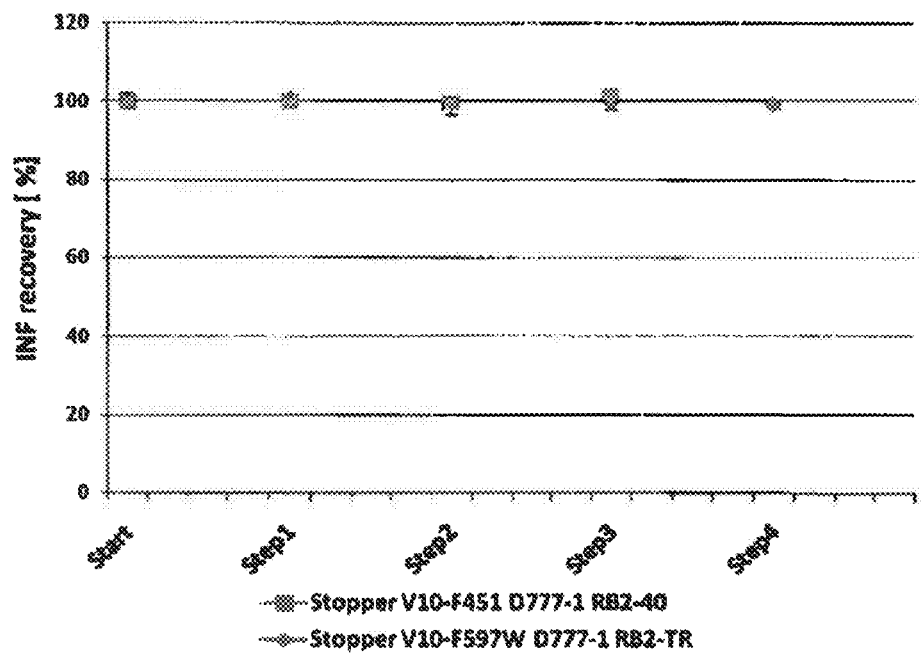
FIG. 12 shows recovery of INF-beta 1a after repeated stopper contact. See formulation study B.

The adsorption of INF-beta 1a to the stoppers (single-vent lyo stopper 20 mm; West Pharmaceutical Services), was examined likewise to the investigation with the siliconized glass vials. The solution was filled into siliconized vials, and the vials were closed using two different types of stoppers. Closed vials were turned upside down to achieve direct contact of the liquid with the stopper. The vials were reversed, after short incubation, and samples were taken. This procedure was repeated four times. The INF-beta 1a content of the samples was analysed using RP-HPLC. The results are shown in FIG. 12. The concentration of INF-beta 1a remains constant after repeated contact to both stoppers. Therefore, by using siliconized stoppers, the adsorption of INF-beta 1a to the stoppers can be prevented.

3. Freeze-Drying Study

In this study it was verified the feasibility of about 31 hours freeze drying cycle for the formulation of lyo solution.

Formulation of Lyo Solution

The INF-beta 1a drug substance (provided by Rentschler Biotechnologie GmbH) was purified via centrifugation (10 min, 4000 rpm) and sterile filtration (0.2 µm) to remove existent insoluble aggregates before compounding was started. The resulting INF-beta 1a concentration was measured by UV spectroscopy (280 nm). The calculation of the INF-beta 1a concentration was based on the extinction coefficient (1.351 mL*µg$^{-1}$*cm$^{-1}$). The excipients, detergents as well as the buffer components were dissolved in WFI in the corresponding ratio (see Table 11). Purified INF-beta 1a drug substance was added to achieve an INF-beta 1a concentration of approximately 17.5 µg/mL in the final lyo solution. Finally the lyo solution was filled up with WFI to the target weight, which was calculated based on the density of the lyo solutions (1.034 g/mL). After sterile filtration using a hydrophilic PVDF membrane, 0.65 resp. 0.725 mL of the lyo solution was filled into hand-siliconized 2R glass type 1 vials.

TABLE 11

Composition of lyo solution.

| | |
|---|---|
| Trehalose dihydrate | 55 g/L |
| Methionine | 0.3 g/L |
| Tween 20 | 1 g/L |
| Tri-sodium-citrate dihydrate | 20.59 g/L |
| Sodium-di-hydrogen phosphate dihydrate | 5.93 g/L |
| Di-sodium-hydrogen phosphate dihydrate | 2.14 g/L |
| INF-β1a | 0.0175 g/L |

Lyophilization Cycle

The lyo solution was freeze-dried by using the lyophilisation cycle showed in Table 12. Samples with and without annealing were compared to each other. Samples without annealing were loaded after the annealing step.

TABLE 12

Lyophilization cycle. After step 5 samples without annealing were loaded.

| | | Shelf temperature [° C.] | Time/Step [h:min] | Total elapsed time [h:min] | Pressure [mbar] | total elapsed time [hours] |
|---|---|---|---|---|---|---|
| | Start | 5 | 00:00 | 0:00:00 | 1000 | 0.00 |
| 1 | Incubation | 5 | 00:30 | 0:30:00 | 1000 | 0.50 |
| 2 | Freezing (ramp) | −40 | 00:30 | 1:00:00 | 1000 | 1.00 |
| 3 | Freezing | −40 | 01:00 | 2:00:00 | 1000 | 2.00 |
| 4 | Annealing (ramp) | −10 | 00:30 | 2:30:00 | 1000 | 2.50 |
| 5 | Annealing | −10 | 04:00 | 6:30:00 | 1000 | 6.50 |
| 6 | Annealing (ramp) | −40 | 00:30 | 7:00:00 | 1000 | 7.00 |
| 7 | Freezing | −40 | 01:00 | 8:00:00 | 1000 | 8.00 |
| 8 | Vacuum | −40 | 00:30 | 8:30:00 | 0.1 | 8.50 |
| 9 | Drying1 | −10 | 01:30 | 10:00:00 | 0.1 | 10.00 |
| 10 | Drying2 | −10 | 10:00 | 20:00:00 | 0.1 | 20.00 |
| 11 | Drying3 | 35 | 05:00 | 25:00:00 | 0.1 | 25.00 |
| 12 | Drying4 | 35 | 06:00 | 31:00:00 | 0.1 | 31.00 |
| | Total | | | 31:00:00 | | 31.00 |

Figure 13:
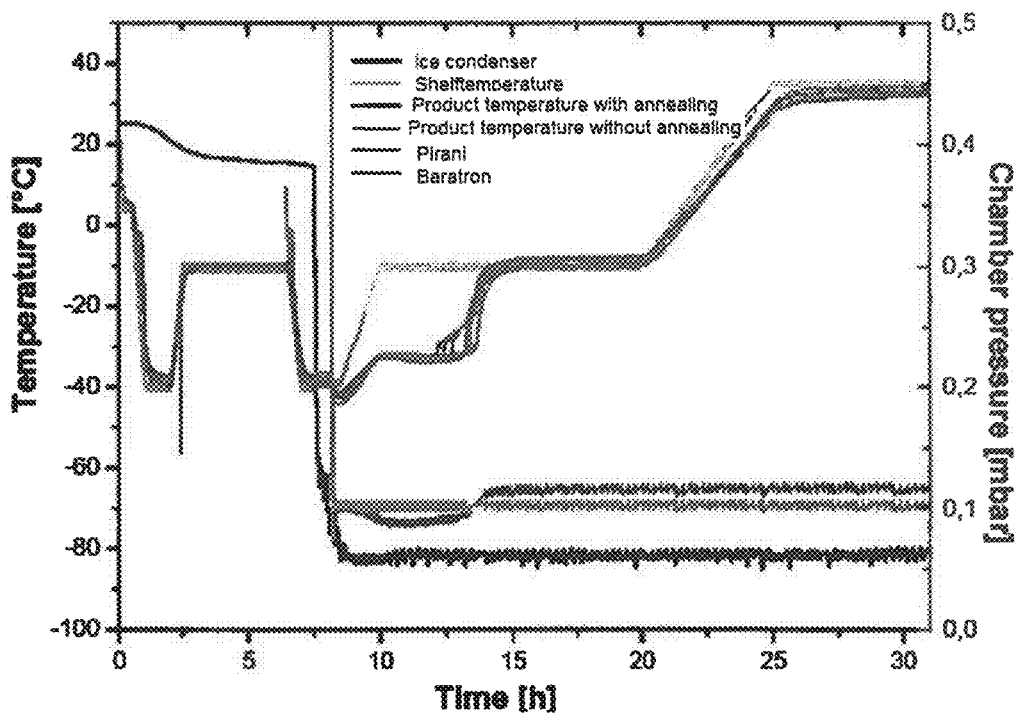
FIG. 13 shows digital data acquisition of the lyo-trial according to freeze-drying study.

FIG. 13 shows the digital data acquisition of the main lyophilisation parameters of the lyophilisation cycle.

Shelf temperature and chamber pressure data prove that the conditions during lyophilisation complied with preset specifications. The product temperature followed the shelf temperature closely during freezing and annealing indicating well defined conditions for the thermal treatment. The progress of the product temperatures of samples with and without annealing was comparable over the whole freeze drying process. The end of primary drying was indicated by a rise of pressure measured by the capacity sensor, which ended after approximately 4.2 hours of primary drying (without ramp).

Imaging

Glass vials were broken and lyophilisates were separated from glass fragments. Lyophilisates were cut vertically using a lancet for imaging of the lyophilisate interior. Pictures were taken of the top surface, bottom surface and cut surface of the lyophilisates. Additionally, transmitted light images were made to identify collapsed structures of the lyophilisate without destroying it.

Figure 14:
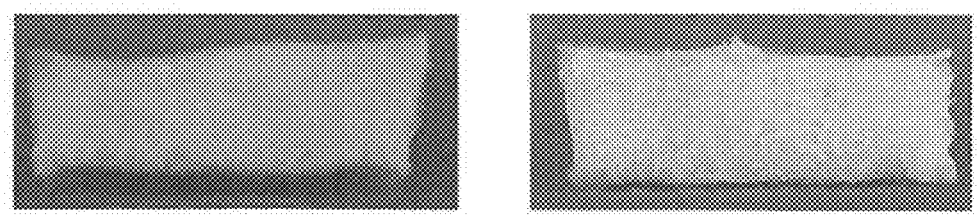
FIG. 14 shows vertical cross-section of lyophilisate. See freeze-drying study.

The vertical cross section of samples with (right) as well as without annealing (left) in FIG. 14 showed no signs of collapse. The crystal structure of both samples was very homogenous and compact.

Figure 15:
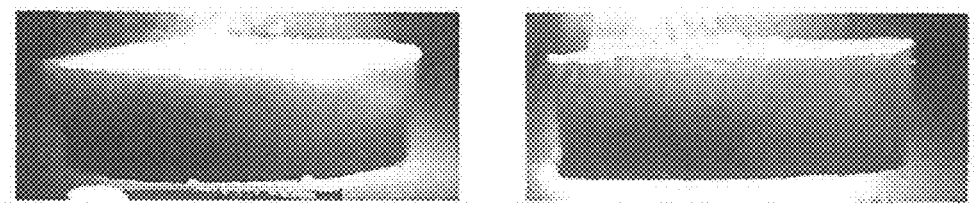
FIG. 15 shows transmitted light image from the edge side of the lyophilisate. See freeze-drying study.

Neither the transmitted light image of samples with annealing (left) nor the transmitted light image of samples without annealing (right) in FIG. 15 revealed any sign of collapse.

Thermal Analysis of the Lyophilisates

Table 13 compares the glass transition temperatures of samples with annealing and samples without annealing.

TABLE 13

Glass transition temperatures of samples.

| | Lyophilisates with annealing | Lyophilisates without annealing |
|---|---|---|
| Glass transition temperature [° C.] | 110 | 96.6 |

Lyophilisates with annealing exhibited a glass transition, which was about 10° C. higher than lyophilisates without annealing. An annealing step increases the porosity of the lyo cakes. Therefore, adsorbed water is more easily removed during secondary drying. Residual water decreases the glass transition temperature, because water as a plasticizer reduces glass transition temperatures in general.

Dissolution Testing

Lyophilisates was reconstituted using a 1 mL syringe. Time required for complete dissolution of the lyophilisate was measured. Table 14 shows dissolution times of lyophilisates with and without annealing.

TABLE 14

Dissolution times of lyophilisates.

| | Dissolution time [sec.] | |
|---|---|---|
| # | Samples with annealing | Samples without annealing |
| 1 | 5 | 39 |
| 2 | 8 | 12 |
| 3 | 10 | 20 |
| 4 | 5 | 15 |
| 5 | 5 | 45 |
| Average | 6.6 | 25.2 |

The reconstitution behaviour was clearly optimized by the annealing step. On an average dissolution time of samples with annealing was approximately 20 sec faster in comparison to samples without annealing.

The parameters for freezing and primary drying of this 31 hours lyo cycle displayed optimal settings for freeze drying of lyophilisates according to the present invention.

4. Stability Study

The stability study investigates the compatibility of lyophilised formulation according to the previous formulation study B with the device and prefilled WFI syringe used in reconstitution and clinical application.

In the compatibility study the MIXJECT™ Transfer Device and prefilled WFI syringes were used for reconstitution of lyopihilized drug product provided in 2R vials. The study provides data for the compatibility of the reconstituted drug product with the vials, with the applied MIXJECT™ Transfer Device and prefilled WFI syringes. The investigation of the stability of the reconstituted drug product was performed after 0 and 24 h storage in the vial and after 24 h storage both in the vial and in the syringe at room temperature (RT) without light protection. In addition, the volume and density of the drug product solution were determined to evaluate if there is a loss of IFN beta-1a from the reconstitution of the drug product up to the administration of the drug solution from the syringe.

The primary packing materials are listed in Table 15 and the materials used for reconstitution and clinical use are described in Table 16.

TABLE 15

Container closure system.

| Material | Material no.(SAP) |
|---|---|
| DIN 2 R siliconized vial | 2000344 |
| Stopper 13 mm 1356 4023/50 Flurotec. B2-TR | 2000188 |
| Flip-off cap, light-blue[#1] | 2000156 |

[#1]Secondary packaging material

TABLE 16

Material for compatibility study.

| Material | Manufacturer | Material no. |
|---|---|---|
| WFI Syringe 1.0 ml. | Vener Pharma International GmbH | 55003229 |
| MIXJECT ™ Transfer Device | West Pharmaceutical Services, Inc. Medimop Medical Projects Ltd. | 9070120 |

The compatibility data resulted from the following analyses: clarity, colour, visible particles, peptide mapping, RP-HPLC, bioassay, SE-HPLC, deamidation, pH-value, osmolality, sub-visible particles and the density and volume of reconstituted drug product at different time points. The acceptance criteria for drug product are listed in Table 17.

TABLE 17

Acceptance criteria for compatibility testing.

| Analytical method | Acceptance criteria |
|---|---|
| *Appearance and description* | |
| Clarity (instumental) | Clear (≤Ref. I) |
| Colour (b-scale, Ph. Eur.) | Report result (Target: Colourless (≤B9)) |
| Colour (y-scale, Ph. Eur.) | Report result (Target: Colourless (< Y7)) |
| Visible particles | Free or practically free of visible particles |
| *Identity* | |
| Peptide Mapping Lys-C | Corresponds to standard |
| *Content* | |
| RP-HPLC content IFN beta-1a protein | Report result (Target: 12.3 ± 2.3 µg/mL) |
| *Activity/Potency* | |
| Bioassay Potency | ≥150 MIU/mg |
| *Purity and impurities* | |
| SE-HPLC HMWS | Report result (Target: ≤2 Area-%) |
| Peptide Mapping Oxidized IFN beta-1a | Report result (Target: ≤6 Area-%) |
| Deamidation | Report result |
| *General tests* | |
| pH | Report result (Target: 6.5 ± 0.2) |
| Osmolality | Report result (Target: 340 ± 50 mOsmol/kg) |
| Sub-visible particles ≥10 µm | ≤6000 particles/container |
| Sub-visible particles ≥25 µm | ≤600 particles/container |

Tables presented in FIGS. 16 to 18 shows compilation of the analytical results for storage at room temperature over 0 hours and 24 hours in the vial and after 24 hours in the syringe and additional 24 hours in the syringe (48 hours value).

As shown in Tables of FIGS. 16 to 18, the results of the compatibility study met all acceptance criteria. In the storage time period the acceptance criteria and target values for clarity, colour and visible particles were fulfilled. The identity of drug product was confirmed in comparison to the corresponding reference standard applying peptide mapping. The elution profile corresponded to that of the reference standard over the whole storage period. The protein content of drug product analysed by RP-HPLC and the Potency analysed by Bioassay fulfilled the target values and acceptance criteria. By SE-HPLC analysis the relative peak area of aggregates was determined to <0.8% (below the reporting level). The degree of oxidized IFN beta-1a in drug product met the target values throughout the study period as determined by peptide mapping. By deamidation analysis it was shown that the degree of deamidated IFN beta-1a in drug product increased from 41.2 Area-% to 48.7 Area-%. The results of pH, osmolality fulfilled the target values. The results of sub-visible particles fulfilled also the acceptance criteria.

In summary the compatibility study shows that lyophilised formulation according to the invention is stable for up to 48 h at room temperature (RT) in the primary packaging material after reconstitution with WFI and having used the MIXJECT™ Transfer Device and prefilled WFI syringe for up to 24 h at room temperature in the primary packaging material used and for up to further 24 h in the syringe.

Determination of Volume of the Solution During the Reconstitution

The intention of measuring the volume of the solution during the three different steps of reconstitution was to determine the loss of protein [μg] during the clinical application (loss from reconstitution of the drug product to delivering the solution from the syringe). The loss during reconstitution was determined by differential weight measurement of the full and empty containers. Together with the density result of the solution, the corresponding volume was calculated. These results are summarized in Tables presented in FIGS. 19 and 20. The volume and density determination of reconstituted drug product was carried out with and without MIXJECT™ Transfer Device.

The determination of volume of the solution during application resulted in the following values: 1.020 mL WFI (density: 0.9981 g/mL) are delivered from the pre-filled syringe. The total volume of the sample solution after reconstitution is 1.026 mL (density: 1.0266 g/mL). 1.011 mL (density: 1.0247 g/mL) reconstituted drug product are delivered from the syringe without the use of the MIXJECT™ Transfer Device and 0.989 mL (density: 1.0252 g/mL) are delivered when using the MIXJECT™ Transfer Device. Along with these values and the content values determined, a loss of 1 μg IFN beta-1a was determined from the time point of reconstitution of the drug product to delivering the solution from the syringe.

5. Bioefficacy Study

The objective of this study was to determine the bioefficacy of lyophilised product of interferon beta-1a, when given by intravenous bolus injection for at least 28 days to cynomolgus monkeys and to provide data to support the use of lyophilised product of interferon beta-1a in humans. The study design is presented in Table 18.

TABLE 18

$^c$FP-1201, i.e. lyophilised product of interferon beta-1a according to the invention, was diluted with 1.068 mL of water for injection to give a nominal concentration of 12.6 μg solution. Each vial was designed to deliver a minimum of 10 μg/mL at 2.3 MIU.

| Group No. | Number of Animals Male | Number of Animals Female | Test Item | Dose Level (MIU/kg/day) | Dose Volume (mL/kg) |
|---|---|---|---|---|---|
| 1 | 3 | 3 | Control | 0 | 1.39 |
| 2 | 3 | 3 | FP-1201$^c$ | 0.25 | 0.12 |
| 3 | 3 | 3 | FP-1201$^c$ | 3.0 | 1.39 |
| 4 | 3 | 3 | FP-1201$^c$ | 1.0 | 0.46 |

Water for injection was used as the control item.

The following parameters and end points were evaluated in this study: pharmacodynamic activity of FP-1201 at different doses, clinical signs, body weights, body weight changes, ophthalmology, electrocardiography, body temperatures, clinical pathology parameters (haematology, coagulation, clinical chemistry, and urinalysis), immunogenicity analysis, gross necropsy findings, organ weights, and histopathology examinations.

There were no clinical observations attributed to treatment.

There were no treatment-related ophthalmic findings and no electrocardiogram or body temperature changes.

There were no changes in urine composition that were attributed to treatment.

Figure 21:
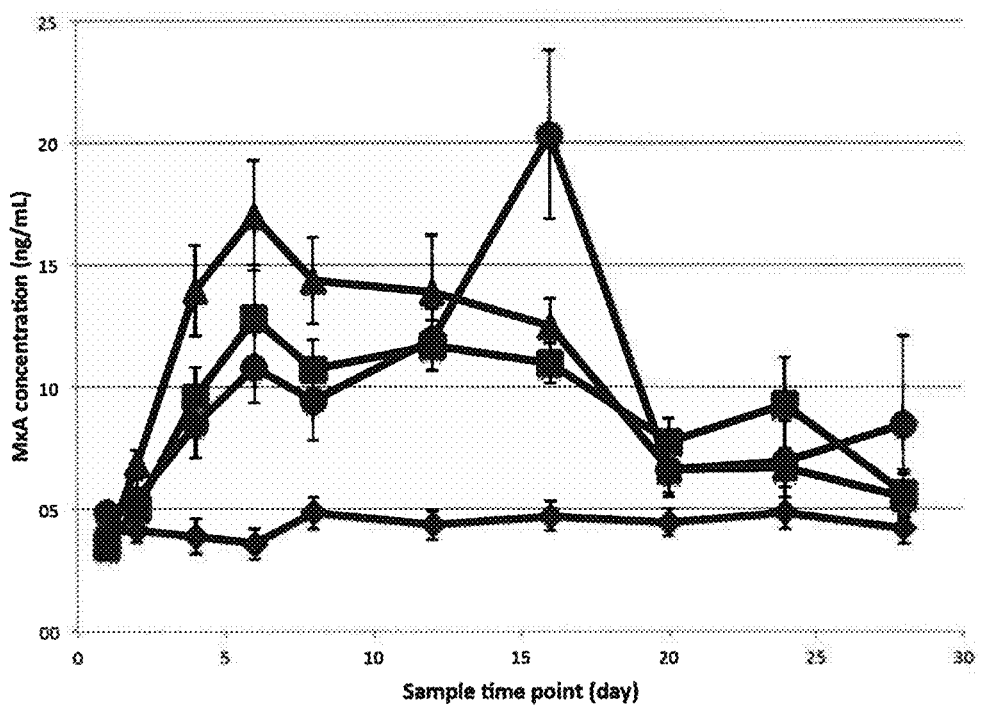
FIG. 21 shows MxA concentration graph of bioefficacy study.

Myxovirus resistance protein A (MxA) is one of the best markers for IFN beta bioactivity and has been widely used in clinical settings for detection of IFN-beta treatment efficacy in Multiple Sclerosis patients. Therefore the MxA were followed in the treated animals. MxA concentrations were induced in all animals treated with IFN beta-1 as expected. All three IFN beta-1 dose levels induced several fold MxA induction in a dose responsive manner. MxA concentrations remained high from Day 6 to Day 16 followed by a gradual decline as presented in FIG. 21 (group 1 (square), group 2 (triangle), group 3 (circle) and group 4 (diamond)). This gradual decrease is most likely due to the development of IFN beta-1 neutralizing antibodies in these animals. The development of neutralizing antibodies against IFN-beta has also been observed in humans after several months or years of IFN-beta treatment of Multiple Sclerosis. Control animals did not show any MxA induction and values remained at baseline concentrations throughout the treatment period. Although higher IFN beta-1 doses induced stronger MxA expression levels clear biological response was also seen using the lowest dose.

There were no organ weight changes or no necropsy or histopathology findings attributed to treatment.

In conclusion, daily intravenous administration of FP-1201 (interferon beta-1a according to the invention) at dose levels of 0.25, 1.0 or 3.0 MIU/kg/day to cynomolgus monkeys for 28 days was associated with an expected increase in MxA induction and was well tolerated. Minor changes in haematology and clinical chemistry parameters and increased neutralising antibody activity were observed on completion of treatment particularly at 3.0 MIU/kg/day.

The invention claimed is:

1. A pharmaceutical formulation in a lyophilised form, comprising unpegylated interferon beta-1a as an active ingredient in an amount of 2.0-15 μg in a single dosage form, a disaccharide as a bulking agent in an amount of 30-50 mg, and a non-ionic surfactant selected from the group consisting of polysorbate and polyethylene glycol, wherein the disaccharide is trehalose dihydrate or a mixture of trehalose dihydrate and sucrose, and wherein the interferon beta-1a is recombinantly produced interferon beta-1a with a biological activity higher than 150 Million International Units (MIU)/mg.

2. The formulation according to claim 1, wherein said formulation further comprises a buffering agent for maintaining a pH of about 5.5 to 7.5 after reconstitution of the lyophilized formulation.

3. The formulation according to claim 1, wherein said disaccharide is trehalose dihydrate.

4. The formulation according to claim 1, wherein said non-ionic surfactant is polysorbate and said disaccharide is trehalose dihydrate.

5. The formulation according to claim 2, wherein said formulation comprises disodium phosphate dihydrate, sodium dihydrogen phosphate dihydrate, trisodium citrate dihydrate or combination thereof as the buffering agent.

6. The formulation according to claim 2, wherein said formulation further comprises an antioxidant.

7. The formulation according to claim 6, wherein said antioxidant is methionine.

8. The formulation according to claim 1, wherein the recombinantly produced interferon beta-1a is recombinant human interferon beta-1a.

9. The formulation according to claim 1, wherein the content of residual moisture of said lyophilisated formulation is not more than 5% by weight.

10. The formulation according to claim 9, wherein the content of residual moisture of said lyophilisated formulation is between 1-5%.

11. The formulation according to claim 1, wherein the formulation is prepared from an aqueous solution having a pH of 5.5-7.5 and comprising
    (i) recombinant human interferon beta-1a as an active ingredient,
    (ii) trehalose dihydrate or a mixture of trehalose dihydrate and sucrose as a bulking agent,
    (iii) polysorbate or polyethylene glycol as a surfactant,
    (iv) a combination of disodium phosphate dihydrate, sodium dihydrogen phosphate dihydrate and trisodium citrate dihydrate as a buffering agent, and
    (v) methionine as an antioxidant.

12. The formulation according to claim 11, wherein the aqueous solution comprises 0.05-0.15% (w/v) polysorbate or polyethylene glycol and 2-6% (w/v) trehalose dihydrate or a mixture of trehalose dihydrate and sucrose.

13. The formulation according to claim 12, wherein said aqueous solution comprises polysorbate.

14. An aqueous pharmaceutical composition obtained by reconstituting a lyophilised formulation of claim 1.

15. The aqueous pharmaceutical composition of claim 14 for intravenous administration.

16. A delivery device comprising the aqueous pharmaceutical composition of claim 14.

17. The delivery device of claim 16, wherein an inner surface of the delivery device is siliconized.

18. A pre-filled syringe comprising the aqueous pharmaceutical composition of claim 14.

19. The pre-filled syringe of claim 18, wherein an inner surface of the pre-filled syringe is siliconized.

20. A method for the treatment of a disease or a disorder which comprises administering a therapeutically effective amount of the lyophilised formulation of claim 1 to a patient in need thereof, wherein the disease or disorder is selected from
    vascular leakage in acute respiratory distress syndrome (ARDS), or systemic inflammatory response syndrome (SIRS),
    ischemia-reperfusion injury in vascular or cardiac surgery and organ transplantation,
    ischemic pre-conditioning prior to major vascular or cardiac surgery and organ transplantation, and
    multi-organ failure (MOF).

21. The method of claim 20, wherein the administration is intravenous administration.

22. A method for the treatment of a disease or a disorder which comprises administering a therapeutically effective amount of the aqueous pharmaceutical composition of claim 14 to a patient in need thereof, wherein the disease or disorder is selected from
    vascular leakage in acute respiratory distress syndrome (ARDS), or systemic inflammatory response syndrome (SIRS),
    ischemia-reperfusion injury in vascular or cardiac surgery and organ transplantation,
    ischemic pre-conditioning prior to major vascular or cardiac surgery and organ transplantation, and
    multi-organ failure (MOF).

23. The method of claim 22, wherein the administration is intravenous administration.

* * * * *